(12) United States Patent
Johnson

(10) Patent No.: US 9,463,180 B2
(45) Date of Patent: Oct. 11, 2016

(54) TREATMENT OF MOLLUSCUM CONTAGIOSUM

(71) Applicant: QUADEX PHARMACEUTICALS, LLC, Midvale, UT (US)

(72) Inventor: B. Ron Johnson, Sandy, UT (US)

(73) Assignee: QUADEX PHARMACEUTICALS, LLC, Midvale, UT (US)

( * ) Notice: Subject to any disclaimer, the term of this patent is extended or adjusted under 35 U.S.C. 154(b) by 1 day.

(21) Appl. No.: 14/211,464

(22) Filed: Mar. 14, 2014

(65) Prior Publication Data

US 2014/0275248 A1    Sep. 18, 2014

Related U.S. Application Data

(60) Provisional application No. 61/781,913, filed on Mar. 14, 2013.

(51) Int. Cl.
| | |
|---|---|
| A61K 33/12 | (2006.01) |
| A61K 31/245 | (2006.01) |
| A61K 31/14 | (2006.01) |
| A61K 45/06 | (2006.01) |
| A61K 31/085 | (2006.01) |
| A61K 31/155 | (2006.01) |
| A61K 31/4425 | (2006.01) |
| A61K 9/00 | (2006.01) |
| A61K 47/10 | (2006.01) |
| A61K 47/18 | (2006.01) |

(52) U.S. Cl.
CPC ........... *A61K 31/245* (2013.01); *A61K 9/0014* (2013.01); *A61K 31/085* (2013.01); *A61K 31/14* (2013.01); *A61K 31/155* (2013.01); *A61K 31/4425* (2013.01); *A61K 45/06* (2013.01); *A61K 47/10* (2013.01); *A61K 47/186* (2013.01)

(58) Field of Classification Search
None
See application file for complete search history.

(56) References Cited

U.S. PATENT DOCUMENTS

| | | |
|---|---|---|
| 1,519,693 A | 12/1924 | Moore |
| 1,822,566 A | 9/1931 | Davies |
| 3,369,543 A | 2/1968 | Ronco |
| 3,620,807 A | 11/1971 | Murray |
| 3,832,460 A | 8/1974 | Kosti |
| 4,176,197 A | 11/1979 | Olson |
| 4,183,684 A | 1/1980 | Avery, Jr. |
| 4,199,574 A | 4/1980 | Schaeffer |
| 4,262,007 A | 4/1981 | Sherrill |
| 4,390,539 A | 6/1983 | Sherrill |
| 4,394,381 A | 7/1983 | Sherrill |
| 4,420,484 A | 12/1983 | Gorman et al. |
| 4,464,398 A | 8/1984 | Sheets et al. |
| 4,486,450 A | 12/1984 | Bernstein |
| 4,507,281 A | 3/1985 | Asculai et al. |
| 4,523,589 A | 6/1985 | Krauser |
| 4,532,128 A | 7/1985 | Sheldon et al. |
| 4,556,557 A | 12/1985 | Reichert |
| 4,599,335 A | 7/1986 | Rentzea et al. |
| 4,661,354 A | 4/1987 | Finnerty |
| 4,745,132 A | 5/1988 | Swered et al. |
| 4,778,813 A | 10/1988 | Fenyes et al. |
| 4,797,420 A | 1/1989 | Bryant |
| 4,820,737 A | 4/1989 | Schoenwald et al. |
| 4,822,605 A | 4/1989 | Powell |
| 4,828,542 A | 5/1989 | Hermann |
| 4,870,108 A | 9/1989 | Page |
| 4,874,794 A | 10/1989 | Katz |
| 4,875,602 A | 10/1989 | Chickering et al. |
| 4,887,994 A | 12/1989 | Bedford |
| 4,895,727 A | 1/1990 | Allen |
| 4,898,888 A | 2/1990 | Baldone |
| 4,902,720 A | 2/1990 | Baldone |
| 4,914,132 A | 4/1990 | Donofrio et al. |
| 4,923,899 A | 5/1990 | Wachman et al. |
| 4,929,442 A | 5/1990 | Powell |
| 4,952,204 A | 8/1990 | Korteweg |
| 4,957,734 A | 9/1990 | Miller |
| 4,975,217 A | 12/1990 | Brown-Skrobot et al. |
| 4,979,420 A | 12/1990 | Cusack |
| 4,983,635 A | 1/1991 | Martin |
| 4,994,199 A | 2/1991 | Scardera et al. |
| 5,008,098 A | 4/1991 | Bernadiner et al. |

(Continued)

FOREIGN PATENT DOCUMENTS

| | | |
|---|---|---|
| CA | 2143136 | 8/1996 |
| CA | 2259709 | 7/1999 |

(Continued)

OTHER PUBLICATIONS

U.S. Appl. No. 13/804,002, filed Mar. 14, 2013, Johnson.

(Continued)

*Primary Examiner* — Jeffrey S Lundgren
*Assistant Examiner* — Michael Schmitt
(74) *Attorney, Agent, or Firm* — Workman Nydegger

(57) ABSTRACT

Methods for treating molluscum contagiosum warts include identifying a human with one or more molluscum contagiosum warts and applying an anti-infective composition to the one or more warts. The anti-infective composition comprises at least one anti-infective agent in a liquid carrier, such as an organohalide. The liquid carrier includes a tissue penetrating component for rapid penetration of the anti-infective agent into the one or more molluscum contagiosum warts. Application of the anti-infective composition to molluscum contagiosum warts causes the warts to turn black and/or fall off the skin in less than about 5 days.

19 Claims, 9 Drawing Sheets

(56) References Cited

U.S. PATENT DOCUMENTS

| | | | |
|---|---|---|---|
| 5,016,651 A | 5/1991 | Stalcup et al. |
| 5,026,561 A | 6/1991 | Bourbon et al. |
| 5,030,659 A | 7/1991 | Bansemir et al. |
| 5,036,095 A | 7/1991 | Andermann |
| 5,039,688 A | 8/1991 | Lewis |
| 5,124,359 A | 6/1992 | Wachman et al. |
| 5,137,724 A | 8/1992 | Balzarini et al. |
| 5,158,766 A | 10/1992 | Greenwald et al. |
| 5,198,217 A | 3/1993 | Vedros |
| 5,284,875 A | 2/1994 | Martin |
| 5,320,805 A | 6/1994 | Kramer et al. |
| 5,338,748 A | 8/1994 | Wachman et al. |
| 5,344,838 A | 9/1994 | Wachman et al. |
| 5,387,611 A | 2/1995 | Rubinstein |
| 5,403,864 A | 4/1995 | Bruch et al. |
| 5,405,602 A | 4/1995 | Simmons et al. |
| 5,439,685 A | 8/1995 | Augros |
| 5,446,014 A | 8/1995 | Schuppiser et al. |
| 5,492,932 A | 2/1996 | Kundsin |
| 5,503,853 A | 4/1996 | Bollen et al. |
| 5,514,640 A | 5/1996 | Jones et al. |
| 5,516,758 A | 5/1996 | Stevens et al. |
| 5,527,534 A | 6/1996 | Myhling |
| 5,531,984 A | 7/1996 | Staats |
| 5,540,934 A | 7/1996 | Touitou |
| 5,580,571 A | 12/1996 | Hostetler |
| 5,631,245 A | 5/1997 | Drube |
| 5,637,307 A | 6/1997 | Simmons et al. |
| 5,661,170 A | 8/1997 | Chodosh |
| 5,678,273 A | 10/1997 | Porcelli |
| 5,704,906 A | 1/1998 | Fox |
| 5,709,866 A | 1/1998 | Booras et al. |
| 5,712,257 A | 1/1998 | Carter |
| 5,725,875 A | 3/1998 | Noll et al. |
| 5,753,270 A | 5/1998 | Beauchamp |
| 5,753,711 A | 5/1998 | Schwabe et al. |
| 5,762,940 A | 6/1998 | Bourbon et al. |
| 5,767,163 A | 6/1998 | Kundsin |
| 5,827,870 A | 10/1998 | Chodosh |
| 5,897,872 A | 4/1999 | Picciano |
| 5,906,814 A | 5/1999 | Epstein |
| 5,922,693 A | 7/1999 | Oldenhove |
| 5,939,461 A | 8/1999 | Siqueira |
| 5,962,391 A | 10/1999 | Oldenhove |
| 5,968,986 A | 10/1999 | Dyer |
| 5,994,383 A | 11/1999 | Dyer et al. |
| 5,997,893 A | 12/1999 | Jampani et al. |
| 6,013,677 A | 1/2000 | Dyer |
| 6,068,851 A | 5/2000 | Bergeron et al. |
| 6,087,400 A | 7/2000 | Dyer et al. |
| 6,165,494 A | 12/2000 | Picciano |
| 6,171,611 B1 | 1/2001 | Picciano |
| 6,187,332 B1 | 2/2001 | Gern et al. |
| 6,211,243 B1 | 4/2001 | Johnson |
| 6,248,343 B1 | 6/2001 | Jampani et al. |
| 6,284,289 B1 | 9/2001 | Van den Berghe |
| 6,329,353 B1 | 12/2001 | Dalrymple et al. |
| 6,342,537 B1 | 1/2002 | Thomsen et al. |
| 6,344,210 B2 | 2/2002 | Fust |
| 6,348,503 B1 | 2/2002 | Squires |
| 6,350,784 B1 | 2/2002 | Squires |
| 6,355,684 B1 | 3/2002 | Squires |
| 6,410,599 B1 | 6/2002 | Johnson |
| 6,414,032 B1 | 7/2002 | Johnson |
| 6,419,850 B1 | 7/2002 | Rouleau |
| 6,420,431 B1 | 7/2002 | Johnson |
| 6,423,750 B1 | 7/2002 | Johnson |
| 6,436,885 B2 | 8/2002 | Biedermann et al. |
| 6,441,045 B1 | 8/2002 | Birnbaum |
| 6,444,707 B1 | 9/2002 | Lampe et al. |
| 6,525,034 B2 | 2/2003 | Dalrymple et al. |
| 6,635,676 B2 | 10/2003 | Baker et al. |
| 6,759,434 B2 | 7/2004 | Johnson |
| 8,173,709 B2 | 5/2012 | Johnson |
| 8,217,080 B2 | 7/2012 | Johnson |
| 8,388,991 B2 | 3/2013 | Sondgeroth et al. |
| 8,470,346 B2 | 6/2013 | Chen |
| 8,598,106 B2 | 12/2013 | Schwarz et al. |
| 9,314,526 B2 | 4/2016 | Johnson |
| 2001/0007651 A1 | 7/2001 | Fust |
| 2002/0006961 A1 | 1/2002 | Katz et al. |
| 2002/0136768 A1 | 9/2002 | Staats |
| 2002/0151521 A1 | 10/2002 | Burke et al. |
| 2002/0161046 A1 | 10/2002 | Konowalchuk et al. |
| 2002/0165277 A1 | 11/2002 | Konowalchuk et al. |
| 2002/0165278 A1 | 11/2002 | Konowalchuk et al. |
| 2002/0188028 A1 | 12/2002 | Johnson |
| 2002/0197212 A1 | 12/2002 | Osbakken et al. |
| 2003/0013769 A1 | 1/2003 | Mukkamala et al. |
| 2003/0077316 A1 | 4/2003 | Nichols et al. |
| 2004/0126333 A1 | 7/2004 | Galli et al. |
| 2004/0258757 A1 | 12/2004 | Bosch et al. |
| 2005/0215639 A1 | 9/2005 | Mohr et al. |
| 2005/0232894 A1 | 10/2005 | Weiner et al. |
| 2006/0019987 A1 | 1/2006 | Fust et al. |
| 2006/0135464 A1 | 6/2006 | Johnson |
| 2007/0054834 A1* | 3/2007 | Baker ............................ 510/504 |
| 2007/0248629 A1 | 10/2007 | Friden et al. |
| 2008/0026013 A1 | 1/2008 | Rabinovich-Guilatt et al. |
| 2008/0260837 A1 | 10/2008 | Namburi et al. |
| 2009/0118168 A1 | 5/2009 | Dinh |
| 2009/0191288 A1 | 7/2009 | Squires |
| 2010/0075914 A1 | 3/2010 | Flack et al. |
| 2011/0076244 A1 | 3/2011 | Hammer |
| 2011/0091556 A1 | 4/2011 | Baker, Jr. et al. |
| 2012/0115812 A1 | 5/2012 | Hammer |
| 2012/0190715 A1 | 7/2012 | Johnson |
| 2012/0219602 A1 | 8/2012 | Flack et al. |
| 2013/0108679 A1 | 5/2013 | Butterfield et al. |
| 2013/0123308 A1 | 5/2013 | Ghannoum et al. |
| 2013/0226107 A1 | 8/2013 | Fields |
| 2014/0364496 A1 | 12/2014 | Johnson |
| 2015/0045443 A1 | 2/2015 | Weaver |
| 2015/0342955 A1 | 12/2015 | Johnson |
| 2015/0374704 A1 | 12/2015 | Johnson |

FOREIGN PATENT DOCUMENTS

| | | |
|---|---|---|
| DE | 4328828 | 3/1995 |
| DE | 69624340 | 6/2003 |
| EP | 0175338 | 3/1986 |
| EP | 181184 | 5/1986 |
| EP | 0190797 | 8/1986 |
| EP | 0308210 | 3/1989 |
| EP | 0357261 | 3/1990 |
| EP | 0478445 | 9/1991 |
| EP | 0487066 | 5/1992 |
| EP | 0872248 | 10/1998 |
| EP | 0937394 | 8/1999 |
| EP | 1023899 | 8/2000 |
| FR | 2700698 | 7/1994 |
| GB | 1479480 | 7/1977 |
| GB | 1574302 | 9/1980 |
| JP | 4 182431 | 6/1992 |
| JP | 61-76401 | 6/1994 |
| JP | 8-164191 | 6/1996 |
| JP | 8-217694 | 8/1996 |
| JP | 10-324624 | 12/1998 |
| WO | WO 94 05258 | 3/1994 |
| WO | WO 95/03734 | 2/1995 |
| WO | WO 96 24367 | 8/1996 |
| WO | WO 97/29742 | 8/1997 |
| WO | WO 97 34607 | 9/1997 |
| WO | WO 98/11778 | 3/1998 |
| WO | WO 98 18474 | 5/1998 |
| WO | WO 98/42188 | 10/1998 |
| WO | WO 99/08713 | 2/1999 |
| WO | WO 99/12545 | 3/1999 |
| WO | WO 99/16447 | 8/1999 |
| WO | WO 01/20981 | 3/2001 |

(56) References Cited

FOREIGN PATENT DOCUMENTS

| WO | WO2004019682 | 3/2004 |
|----|--------------|--------|
| WO | WO2004050059 | 6/2004 |

OTHER PUBLICATIONS

U.S. Appl. No. 09/669,068, filed Sep. 22, 2000, Johnson.
U.S. Appl. No. 09/669,067, filed Sep. 22, 2000, Johnson.
U.S. Appl. No. 09/668,950, filed Sep. 22, 2000, Johnson.
AHFS Drug Information pp. 3107-3108 1999.
J.S. Armstrong and E.J. Froelich—Inactivation of Viruses by Benzalkonium Chloricle—Applied.
Berti et al. Transcutaneous Drug Delivery: A Practical Review Mayo Clin. Proc. vol. 70 pp. 581-586 Jun. 1995.
Choi et al. The Pretreatment Effect of Chemical Skin Penetration Enhancers in Transdermal Drug Delivery Using Iontophoresis Skin Pharmacol. Appl. Skin.
Comfort et al. Enhanced Transport in a Therapeutic Transdermal System Biomaterials vol. 11 No. 9 pp. 729-733 Nov. 1990.
De Clercq, "Recent highlights in the development of new antiviral drugs", Current Opinion in Microbiology (2005), vol. 8, pp. 552-560.
Encyclopedia of Chemistry, vol. 1, ed. Editorial committee for Encyclopedia of Chemistry, Kyoritsu Shuppan Co. Ltd, Feb. 15, 1987, p. 888.
Fang et al. Development and Evaluation on Transdermal Delivery of Enoxacin Via Chemical Enhancers and Physical Iontophoresis Journal of Controlled Release.
Gismondo et al. Efficacia Antimicrobica e Sporicida di Varie Soluzioni Disinfettanti Minerva Medica (Italy) vol. 86 pp. 21-32 Jan.-Feb. 1995 (English translation attached: Antimicrobial and Sporicidal Efficacy of Some Disinfectant Solutions).
James Alexander Corporation flyer Medicaine® Topical Antiseptic 1997.
James Alexander Corporation flyer Medicaine® Sting and Bite Relief Formula Flyer 1997.
James Alexander Corporation flyer Unit Dose Swabs 1997.
Jin et al. Effect of Application vol. of Ethanol-Isopropyl Myristate Mixed Solvent System on Permeation of Zidovudine and Probenecid Through Rat Skin Drug.
Johnson et al. Synergistic Effects of Chemical Enhancers and Therapeutic Ultrasound on Transdermal Drug Delivery Journal of Pharmaceutical Sciences vol. 85 No. 7 pp. 670-679 Jul. 1996.
Kanikkannan et al. Structure-Activity Relationship of Chemical Penetration Enhancers in Transdermal Drug Delivery Current Medicinal Chemistry vol. 7 No. 6.
Kunta, J. R. et al., "Effect of mentol and related terpenes on the percutaneous absorption of propanol across excised hairless mouse skin", Journal of Paharmaceutical Science vol. 86, No. 12, pp. 1369-1373, Dec. 1997.
Kurokawa et al., "Efficacy of traditional herbal medicines in combination with acyclovir against herpes simplex virus type 1 infection in vitro and in vivo", Antiviral Research (1995), vol. 27, pp. 19-37.
Martindale The Extra Pharmacopoeia Benzethonium Chloride/Benzyl Alcohol p. 1119 Royal Pharmaceutical Society 1996.
Martindale The Extra Pharmacopoeia Disinfectants and Preservatives pp. 1114-1116 Royal Pharmaceutical Society 1996.
Martindale The Extra Pharmacopoeia Ethyl Hydroxybenxoate/Magenta p. 1137 Royal Pharmaceutical Society 1996.
Martindale The Extra Pharmacopoeia Local Anesthetics pp. 1317 1320-1321 Royal Pharmaceutical Society 1996.
The Merck Index An Encyclopedia of Chemicals drugs and Biologicals Twelfth Edition pp. 177 and 180 1996.
Meyler's Side Effects of Drugs an Encyclopedia of Adverse Reactions and Interactions Antiseptic Drugs and Disinfectants Chapter 24 pp. 643-644 and 664-665 1996.
Neyts et al., "The Novel Immunosuppressive Agent Mycophenolate Mofetil Markedly Potentiates the Antiherpesvirus Activities of Acyclovir, Ganciclovir, and Penciclovir in vitro and in Vivo", Antimicrobial Agents and Chemotherapy (1998), vol. 42, pp. 216-222.
Neyts et al., "Mycophenolate mofetil strongly potentiates the antiherpesvirus activity of acyclovir", Antiviral Research (1998), vol. 40, pp. 53-56.
Remington's Pharmaceutical Sciences, 15th Edition, 1975, Mack Publishing Co. p. 685.
Sanofi Pharmaceuticals Inc. Zephiran® Chloride Brand of Benzalkonium Chloride 1997.
Satyaprakash et al., Viremia in Acute Herpes Zoster, JID 2009:200 (Jul. 1, 2009), pp. 26-32 Dowlnloaded from http://jid.oxfordjournals.org/ Feb. 16, 2015.
Williams et al. Skin Absorption Enhancers Critical Reviews in Therapeutic Drug Carrier Systems 9(34) pp. 305-353 1992.
Wu et al. In Vitro Effect of Penetration Enhancers on Sodium Nonivamide Acetate in Rat Skin Biol. Pharm. Bull. vol. 18 No. 12 pp. 1790-1792 1995.Williams et al. Skin Absorption Enhancers Critical Reviews in Therapeutic Drug Carrier Systems 9(34) pp. 305-353 1992.
Zatz, L. J. "Enhancing Skin Penetration of Actives with the Vehicle", Cosmetics and Toiletries, vol. 109, Sep. 1994, p. 27-36.
Zatz, L. J. Modification of Skin Permeatation by Solvents, Cosmetics and Toiletries vol. 106, Feb. 1991, p. 91-98.
U.S. Appl. No. 09/401,076, filed Aug. 3, 2000, Office Action.
U.S. Appl. No. 09/401,076, filed Nov. 1, 2000, Notice of Allowance.
U.S. Appl. No. 09/668,949, filed Sep. 13, 2001, Office Action.
U.S. Appl. No. 09/668,950, filed Sep. 13, 2001, Office Action.
U.S. Appl. No. 09/668,951, filed Sep. 21, 2001, Office Action.
U.S. Appl. No. 09/668,953, filed Sep. 25, 2001, Office Action.
U.S. Appl. No. 09/669,067, filed Sep. 25, 2001, Office Action.
U.S. Appl. No. 09/669,068, filed Sep. 27, 2001, Office Action.
U.S. Appl. No. 09/993,178, filed Jan. 15, 2002, Office Action.
U.S. Appl. No. 09/668,951, filed Feb. 26, 2002, Notice of Allowance.
U.S. Appl. No. 09/669,068, filed Feb. 26, 2002, Notice of Allowance.
U.S. Appl. No. 09/668,953, Mar. 4, 2002, Notice of Allowance.
U.S. Appl. No. 09/993,178, filed Mar. 26, 2002, Notice of Allowance.
U.S. Appl. No. 10/200,897, filed Aug. 20, 2003, Office Action.
U.S. Appl. No. 10/200,897, filed Jan. 16, 2004, Notice of Allowance.
U.S. Appl. No. 11/348,127, filed Oct. 4, 2007, Office Action.
U.S. Appl. No. 10/816,571, filed Nov. 28, 2007, Office Action.
U.S. Appl. No. 11/348,127, filed Feb. 29, 2008, Office Action.
U.S. Appl. No. 10/816,571, filed May 22, 2008, Office Action.
U.S. Appl. No. 10/816,571, filed Sep. 17, 2009, Office Action.
U.S. Appl. No. 10/816,571, filed Mar. 30, 2010, Office Action.
U.S. Appl. No. 10/816,571, filed Dec. 21, 2010, Office Action.
U.S. Appl. No. 10/816,571, filed Jul. 21, 2011, Office Action.
U.S. Appl. No. 13/157,210, filed Oct. 28, 2011, Office Action.
U.S. Appl. No. 10/816,571, filed Nov. 28, 2011, Final Office Action.
U.S. Appl. No. 10/816,571, filed Dec. 28, 2011, Notice of Allowance.
U.S. Appl. No. 13/157,210, filed Mar. 20, 2012, Notice of Allowance.
U.S. Appl. No. 13/012,719, filed Feb. 15, 2013, Office Action.
U.S. Appl. No. 13/012,719, filed Mar. 21, 2014, Final Office Action.
U.S. Appl. No. 13/012,719, filed May 30, 2014, Notice of Allowance.
U.S. Appl. No. 13/804,002, filed Jul. 17, 2014, Office Action.
U.S. Appl. No. 13/804,002, filed Jan. 28, 2015, Final Office Action.
U.S. Appl. No. 14/466,625, filed Jul. 24, 2015, Office Action.
U.S. Appl. No. 14/466,637, filed Jul. 24, 2015, Office Action.
U.S. Appl. No. 13/804,002, filed May 8, 2015, Notice of Allowance.
U.S. Appl. No. 14/466,625, filed Dec. 18, 2015, Notice of Allowance.
U.S. Appl. No. 14/823,830, filed Dec. 30, 2015, Office Action.
U.S. Appl. No. 14/466,637, filed Feb. 11, 2016, Final Office Action.

\* cited by examiner

TREATMENT OF MOLLUSCUM CONTAGIOSUM

CROSS-REFERENCE TO RELATED APPLICATIONS

The present application claims the benefit of U.S. Patent Application Ser. No. 61/781,913, filed Mar. 14, 2013, entitled "TREATMENT OF MOLLUSCUM CONTAGIOSUM", the disclosure of which is incorporated by reference in its entirety.

BACKGROUND OF THE INVENTION

1. The Field of the Invention

The invention relates to method of treating molluscum contagiosum warts.

2. The Relevant Technology

Molluscum contagiosum is a viral infection of the skin or occasionally of the mucous membranes, sometimes called water warts. It is caused by a DNA poxvirus called the molluscum contagiosum virus (MCV). MCV has no non-human-animal reservoir and infects only humans). There are four types of MCV, MCV-1 to -4; MCV-1 is the most prevalent and MCV-2 is seen usually in adults and often sexually transmitted. This common viral disease has a higher incidence in children, sexually active adults, and those who are immunodeficient. The infection is most common in children aged one to ten years old. MC can affect any area of the skin but is most common on the trunk of the body, arms, and legs. It is spread through direct contact or by shared items such as clothing or towels. Worldwide, Approximately 122 million people were affected by molluscum contagiosum as of 2010 (1.8% of the population).

The virus commonly spreads through skin-to-skin contact. This includes sexual contact or touching or scratching the bumps and then touching the skin. Handling objects that have the virus on them (fomites), such as a towel, can also result in infection. The virus can spread from one part of the body to another or to other people. The virus can be spread among children at day care or at school. Molluscum contagiosum is contagious until the bumps are gone (which, if untreated, may last up to 6 months or longer).

The time from infection to the appearance of lesions can range up to 6 months, with an average incubation period between 2 and 7 weeks. A person infect with Molluscum contagiosum can have one or many warts on one or more parts of the body. In some cases, dozens or even hundreds of unsightly warts can be seen up and down a person's arms and legs. Molluscum contagiosum lesions are flesh-colored, dome-shaped, and pearly in appearance. They are often 1 to 5 millimeters in diameter, with a dimpled center. They are generally not painful, but they may itch or become irritated. Picking or scratching the bumps may lead to further infection or scarring. In about 10% of the cases, eczema develops around the lesions. They may occasionally be complicated by secondary bacterial infections. In some cases the dimpled section may bleed.

The viral infection is limited to a localized area on the topmost layer of the epidermis. Once the virus-containing head of the lesion has been destroyed, the infection is gone. The central waxy core contains the virus. In a process called autoinoculation, the virus may spread to neighboring skin areas when the infected person touches the affected area and then touches an unaffected area. Children are particularly susceptible to autoinoculation, and may have widespread clusters of lesions.

Individual molluscum lesions may go away on their own and are reported as lasting generally from 6 weeks to 3 months. The lesions may propagate via autoinoculation so an outbreak generally lasts longer. Mean durations for an outbreak are variously reported from 8 months to about 18 months, but durations are reported as widely as 6 months to 5 years, lasting longer in immunosuppressed individuals.

Histologically, molluscum contagiosum is characterized by molluscume bodies in the epidermis above the stratum basale, which consist of large cells with abundant granular eosinophilic cytoplasm (accumulated virons) and a small peripheral nucleus.

Although treatment may sometimes be unnecessary, no single approach has been convincingly shown to be effective. It should also be noted that treatments which cause the skin on or near the lesions to rupture may spread the infection further, much like scratching does. In some cases, astringent chemicals can be applied to the surface of molluscum lesions to destroy successive layers of the skin. Examples include potassium hydrochloride, and cantharidin. For mild cases, over-the-counter wart medicines, such as salicylic acid may or may not shorten infection duration. Daily topical application of tretinoin cream may also trigger resolution. These treatments typically require several months for the infection to clear, and are often associated with intense inflammation and possibly discomfort. Given the slowness and ineffectiveness of such "treatments," pediatricians and dermatologists often advise their clients that there is no known cure for molluscum contagiosum, although some have advised using tea tree oil to relieve symptoms, such as itching or burning.

Imiquimod has also been used with minimal success. Imiquimod is a form of immunotherapy. Immunotherapy triggers the immune system to fight the virus causing the skin growth. Imiquimod is applied 3 times per week, left on the skin for 6 to 10 hours, and washed off. A cure may take from 4 to 16 weeks. Small studies have indicated that it is successful about 80% of the time. Another dose regimen includes applying imiquimod three times daily for 5 consecutive days each week. Given the lengthiness of such treatments, they are largely ineffective unless the patient is highly motivated and very patient.

Surgical treatments include cryosurgery, in which liquid nitrogen is used to freeze and destroy lesions, as well as scraping them off with a curette. Application of liquid nitrogen may cause burning or stinging at the treated site, which may persist for a few minutes after the treatment. Scarring or loss of color can complicate both these treatments. With liquid nitrogen, a blister may form at the treatment site, but it will slough off in two to four weeks. Although its use is banned by the FDA in the United States in its pure, undiluted form, the topical blistering agent cantharidin can be effective. Although cryosurgery and curette scraping are relatively "painless" procedures, they can leave scars and/or permanent white (depigmented) marks.

Pulsed dye laser therapy may be used for cases that are persistent and do not resolve following other measures. As of 2009, however, there is no evidence that laser treatment is efficacious for genital lesions.

Most cases of molluscum contagiosum will clear up naturally within two years (usually within nine months). However, so long as the skin growths are present, there is a possibility of transmitting the infection to another person. When the growths are gone, the possibility for spreading the infection is ended.

Unlike herpes viruses, which can remain inactive in the body for months or years before reappearing, molluscum contagiosum does not remain in the body when the growths are gone from the skin and will not reappear on their own. However, there is no permanent immunity to the virus, and it is possible to become infected again upon exposure to an infected person.

If left untreated, molluscum growth can reach sizes as large as a pea or a marble. Spontaneous resolution of large lesions can occur, but will leave larger crater-like growth. As many treatment options are available, prognosis for minimal scarring is best if treatment is initiated while lesions are small.

SUMMARY

Disclosed herein are methods for treating molluscum contagiosum warts. Example methods include: (1) identifying a human with one or more molluscum contagiosum warts; and (2) applying an anti-infective composition to the one or more warts.

According to one embodiment, the anti-infective composition includes at least one anti-infective agent in a liquid carrier. The anti-infective agent advantageously includes one more organohalides (e.g., at least one quaternary ammonium chloride compound, such as benzalkonium chloride). The liquid carrier advantageously includes a tissue penetrating component (e.g., isopropyl alcohol in water) for rapid penetration of the anti-infective agent into the one or more molluscum contagiosum warts.

Even though existing treatments can take weeks or months to be effective, if at all, application of anti-infective compositions as disclosed herein can causes the one or more molluscum contagiosum warts to turn black and/or fall off the skin in a matter of days (e.g., 10 days or less, preferably 7 days or less, more preferably 5 days or less, most preferably 3 days or less).

Although molluscum contagiosum warts are generally not painful, they can itch or otherwise cause discomfort. To further relieve discomfort associated with molluscum contagiosum warts and enhance treatment success (e.g., prevent scratching to spread the virus, the anti-infective composition can further include a topical anesthetic, such as benzocaine. Depending on the concentration, the benzocaine can further enhance penetration of the anti-infective composition into the one or more molluscum contagiosum warts.

Unlike common wart medicines, which can leave a layer of wax-like composition on the surface, or tea tree oil, which can leave an oily surface, the anti-infective composition can be formulated according to one embodiment so as to not be visibly detectable on the one or more molluscum contagiosum warts within about 1 minute or less after application. Moreover, in one embodiment, the anti-infective composition may contain less than 10% of oils (e.g., tea tree oil) or may be substantially or totally free of oils.

These and other advantages and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF DISCLOSED EMBODIMENTS

Disclosed herein are methods for treating molluscum contagiosum warts. According to several embodiments of the invention, example methods may include: (1) identifying a human with one or more molluscum contagiosum warts and (2) applying an anti-infective composition to the one or more warts. Even though existing treatments can take weeks or months to be effective, if at all, application of anti-infective compositions as disclosed herein can causes the one or more molluscum contagiosum warts to turn black and/or fall off the skin in a matter of days (e.g., 10 days or less, preferably 7 days or less, more preferably 5 days or less, most preferably 3 days or less).

Figure 1:
FIG. 1 is a photograph of an arm with an outbreak of unsightly molluscum contagiosum warts all over it.

FIG. 1 illustrates an outbreak of molluscum contagiosum warts on a person's arm. The warts are pinkish, raised and generally unsightly. They are also highly contagious even if not fatal to the person or potentially infected person. Such warts can be transmitted sexually, which can be extremely devastating to the person with such warts as well as potential partners who might be infected with such warts.

According to one embodiment, the anti-infective composition includes at least one anti-infective agent in a liquid carrier. The anti-infective agent advantageously includes one more organohalides (e.g., at least one quaternary ammonium chloride compound, such as benzalkonium chloride). The liquid carrier advantageously includes a tissue penetrating component (e.g., isopropyl alcohol in water) for rapid penetration of the anti-infective agent into the one or more molluscum contagiosum warts.

As a result of high penetration of the anti-infective composition, effective relief from the discomfort and effects of molluscum contagiosum warts can often be achieved after only a single application to the warts and, in many cases, in 5 applications or less, preferably 4 applications or less, and most preferably in 2 or 3 applications or less. The anti-infective composition is preferably absorbed into the molluscum contagiosum warts to such an extent that in less than 1 minute after application the composition can no longer be seen or felt (i.e., the treatment area looks dry and feels dry to the touch). Preferably, the anti-infective composition is essentially completely absorbed into the warts in less than about 40 seconds, more preferably in less than about 30 seconds, even more preferably in less than about 20 seconds, and most preferably in less than about 10 seconds.

The anti-infective composition preferably penetrates through the skin into the nucleus of the molluscum contagiosum wart in order to kill the virus causing the skin disorder. Application of pressure may further increase the ability of the anti-infective composition to penetrate, as pressure may flatten or compress the tissue of the wart and assist in forcing the anti-infective composition downward through the warty tissue. In any event, penetration to the nucleus is rapidly accomplished, preferably in several seconds, mainly as a result of the tissue penetrating effect of the liquid carrier system, such a mixture of water and one or more of isopropyl alcohol, ethanol, acetone, and the like.

While the anti-infective composition rapidly penetrates to the nucleus, it is also postulated that the anti-infective composition can collect in the nucleus without penetrating into healthy skin below the molluscum contagiosum wart over an extended period of time. Pressure may assist in displacing interstitial fluid held within the wart nucleus, which may then be replaced with anti-infective composition. When the wart nucleus is filled with the anti-infective composition, the anti-infective composition is available as a bath that continues to deactivate viruses as it slowly diffuses throughout the wart. On this basis, it is desirable to deliver a large quantity of treatment composition into the warty tissue such that the nucleus is saturated for a period that enables the anti-infective composition to achieve its virus deactivation purpose before it diffuses into the body.

For example, the volume of anti-infective composition applied to a typical molluscum contagiosum wart may be in range from about 0.2 ml to about 1 ml, preferably in range of about 0.3 ml to about 0.9 ml, more preferably in range of about 0.4 ml to about 0.8 ml, and most preferably in a range of about 0.5 ml to about 0.7 ml.'

The anti-infective compositions include at least a biologically active agent and a liquid carrier that enhances penetration of the anti-infective composition into warty tissue caused by molluscum contagiosum. The biologically active agent is selected so as to be effective in treating warts caused by the molluscum contagiosum virus. The liquid carrier is selected to optimally enable the anti-infective composition to penetrate into the wart, including the nucleus where the viruses replicate. Biologically active agents suitable for use in anti-infective compositions are set forth hereinbelow and the liquid carriers are described thereafter.

Biologically active agents are preferably anti-infective quaternary ammonium halides and organic compounds that contain at least one carbon-halogen bond. These anti-infective compounds are referred to herein collectively as organohalides, even though some of the anti-infective compounds of this invention do not contain a carbon-halogen bond. Biologically active agents included in anti-infective compositions used herein comprise anti-viral organohalides. Benzalkonium chloride is a preferred organohalide. However, other organohalides or quaternary ammonium halide compounds may be used as the active agents in the compositions. Other active agents that are organohalides may include organo-bromides and organo-iodides. Preferably, the organohalides have an alkyl group attached thereto such as a simple $C_nH_{2n+1}$ chain, where n is in a range from 1 to about 50.

The generic chemical structure of benzalkonium chloride is shown below:

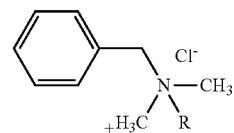

where $R=C_8H_{17}$ to $C_{18}H_{37}$.

As shown, benzalkonium chloride includes a benzene ring and a nitrogen constituent (i.e., a quaternary ammonium group) near the ring. A carbon atom is disposed between the nitrogen constituent and the benzene ring. Two methyl groups and an R group of varying size extend from the nitrogen atom. Suitable benzalkonium chloride may be obtained from many suppliers for example, Spectrum of Gardena, Calif.; Stepan of Northfield, Ill.; Sanofit Pharmaceuticals, Inc. of New York, N.Y. and Mason Chemical of Arlington Heights, Ill.

The term "benzalkonium chloride" as used herein includes compounds in which the alkyl group chain length is within a wide range. A preferred embodiment involves a mixture of compounds with an alkyl chain length distribution that is about 40% $C_{12}$, about 50% $C_{14}$, and about 10% $C_{16}$ (CAS Reg. No. 68424-85-1). Examples of such products include Maquat MC-1412-50%, Mason Chemical Company, 50% activity; Maquat MC-1412-80%, Mason Chemical Company, 80% activity; and BTC-835, Stepan Company, 50% activity. While the foregoing examples satisfy the US Pharmacopoeia requirements for alkyl chain distribution, other alkyl chain distributions are effective against the target lipid coated viruses and other target pathogens. These embodiments are also contemplated within the scope of this invention. These ranges include about 1%-99% $C_{12}$, about 1%-99% $C_{14}$, and about 1%-99% $C_{16}$. and optionally about 1%-99% $C_{18}$. Each manufacturer publishes methods to analyze the bulk substance. Notwithstanding the fact that benzalkonium chloride often refers to mixtures of compounds of varying alkyl chain length, it should be understood that it is within the scope of the invention to utilize a singular benzalkonium chloride compound comprising only one alkyl chain of a particular length.

These anti-infective agents, particularly benzalkonium chloride, are highly effective in killing viruses that cause molluscum contagiosum. Also, these anti-infective agents can neutralize or eliminate toxins and inflammatory agents caused by such viruses. Rapidly eliminating or neutralizing toxins, inflammatory agents, and their sources results in prompt relief of itching or discomfort, which can increase efficacy of treatment by reducing the urge to scratch.

Benzalkonium bromide and benzalkonium iodide are also examples of suitable organohalides. Benzalkonium bromide has the structure of benzalkonium chloride with the difference being that the chlorine is substituted with a bromine constituent. Analogous considerations apply to benzalkonium iodide. Another example of a suitable organohalide is cetyl trimethylammonium bromide.

Examples of other organochlorides which have anti-infective properties include benzethonium chloride, methyl benzethonium chloride, cetyl pyridinium chloride, chloroxylenol, hexachlorophene, triclosan, and chlorhexidine. Additional examples of organohalides, more particularly quaternary ammonium halides having an alkyl with 6-18 carbons, include: alkyl benzyl dimethyl ammonium halide, alkyl dimethyl ethyl benzyl ammonium halide, n-alkyl dimethyl benzyl ammonium halide, diisobutyl phenoxy ethoxy ethyl dimethyl benzyl ammonium halide, n-($C_{12}C_{14}C_{16}$) alkyl dimethyl benzyl ammonium halide, dodecyl dimethyl ammonium halide, dioctyl dimethyl ammonium halide, dialkyl dimethyl ammonium halide, dialkyl methyl benzyl ammonium halide, octyl decyl dimethyl ammonium halide, lauryl dimethyl benzyl ammonium halide, o-benzyl-p-chlorophenol, dideryl dimethyl ammonium halide, dioctyl dimethyl ammonium halide, and alkyl ($C_{14}C_{12}C_{16}$) dimethyl benzyl ammonium halide.

Additional examples of effective organohalides include dual quaternary ammonium compounds comprising at least two quaternary ammonium compounds. One of such embodiments comprises a mixture of n-alkyl dimethyl benzyl ammonium halide and n-dialkyl methyl benzyl ammonium halide. An example is distributed by Stepan as BTC7 776, with a chain length distribution for the n-alkyl of about 60% $C_{14}$, about 30% $C_{16}$, about 5% $C_{12}$, and about 5% $C_{18}$ (CAS Reg. No. 683991-10-5), and a chain length distribution for the n-dialkyl of about 60% $C_{14}$, about 30% $C_{16}$, about 5% $C_{12}$, and about 5% $C_{18}$ (CAS Reg. No. 68391-05-9). Another example comprises a mixture of n-alkyl dimethyl benzyl ammonium halide (I) and n-alkyl dimethyl ethyl benzyl ammonium halide (II). An example is distributed by Stepan as BTC 21257M series with a chain length distribution for the n-alkyl in entity (I) of about 60% $C_{14}$, about 30% $C_{16}$, about 5% $C_{12}$, and about 5% $C_{18}$ (CAS Reg. No. 683991-10-5), and a chain length distribution in entity (II) of about 68% $C_{12}$, and about 32% $C_{14}$ (CAS Reg. No. 68956-79-6).

A preferred method of preparing an anti-infective composition involves taking 70% isopropyl rubbing alcohol USP (70% isopropanol, v/v, specific gravity 0.877 at 20 C, see 35 USP, p. 357) and then admixing the organohalide. Isopropyl alcohol USP (IPA) is available from any number of US sources, including Union Carbide, Aldrich Chemical, Texaco, and Shell. Purified water USP is available from a variety of laboratory supply houses, such as Aldrich Chemical, Fisher Scientific, and VWR Scientific. Purified water USP can also be obtained by means of a commercially available water purification system designed to meet the requirements of Purified Water USP.

Embodiments include organohalide concentrations in a range of about 0.001% to about 2% by weight of the anti-infective composition. These concentration values also refer to preparations that include benzalkonium chloride and where the active ingredient is not benzalkonium chloride, but one of the other substances herein disclosed as active ingredients and equivalents thereof. Furthermore, these concentration values also refer to the combined amounts of active ingredients when more than one active ingredient is present in other embodiments according to this invention, such as when the composition comprises dual quaternary ammonium compounds.

When the anti-infective agent is benzalkonium chloride or other aromatic quaternary ammonium halide compound, the concentration within a topical composition can be in a range of about 0.01% and to about 0.5% by weight of the composition, more preferably in a range from about 0.05% to about 0.3% by weight of the composition, and most preferably in a range from about 0.1% to about 0.2% by weight of the composition. To avoid toxicity, the concentration can be less than 0.26% by weight and is preferably about 0.13% by weight of the anti-infective composition.

In one embodiment, the anti-infective composition consists essentially of the active agent, such as benzalkonium chloride, and the liquid carrier, and optionally, benzocaine. In other embodiments, the treatment composition consists essentially of the active agent, liquid carrier, and benzocaine, together with other components as described hereinbelow. The liquid carrier is preferably sufficiently inert with respect to the active agent and any other component present to enable the treatment composition to be stored for long periods of time without deactivating the anti-infective agent, such as at least 1 year and preferably at least 2 or more years.

The liquid carrier preferably has properties that enhance the ability of the treatment composition to penetrate into the warty tissue of molluscum contagiosum. The carrier may have a viscosity and/or density which is not significantly greater than that of water in order to optimally enable the treatment composition to penetrate into the warty tissue. Using a carrier composition having a viscosity which is not significantly greater than water is in contrast to compositions that are coated onto afflicted tissue. Accordingly, anti-infective compositions used herein may exclude formulations which may be considered to be primarily or essentially gels, creams, lotions, oils, ointments, pastes, emulsions, and viscous colloidal suspensions.

The carrier preferably has a tissue penetrating component, such as isopropyl alcohol, that is capable of penetrating molluscum contagiosum warts in a rapid manner. The anti-infective composition enables the warty tissue to be saturated in the region of the nucleus for a period that enables the anti-infective composition to achieve its purpose of deactivation of molluscum contagiosum viruses before it diffuses into the body. In this way, the composition can form a temporary reservoir (or bath) in the nucleus of the molluscum contagiosum warts where it is needed most. In this way, the anti-infective composition can maximize its effect of deactivation of viruses and/or destroying toxins within the warts while minimizing possible damage to surrounding healthy tissues or the organism as a whole.

While isopropyl alcohol is a preferred carrier, other alcohols may also be used. In addition to isopropyl alcohol, ethanol and methanol are also suitable carriers. Benzyl alcohol can be used as a carrier or as an additive as it also acts as a bacteriostat and an anesthetic. Acetone can also be used. Mixtures of the above-mentioned solvents may also be used as desired depending upon the application. As indicated above, however, isopropyl alcohol or ethyl alcohol is preferably used in combination with other carrier constituents. For example, water may be added to isopropyl alcohol to reduce pain or discomfort which may be felt when only isopropyl alcohol is used. Similarly, isopropyl alcohol may be utilized with cetyl alcohol or a combination of cetyl, stearyl, myristyl, or lauryl alcohol and water to reduce the sensation.

Carriers that include isopropyl alcohol and water can have varying ratios depending on the intended use. However, for treating molluscum contagiosum warts, the water is preferably included in a range from about 10% to about 50% by volume of the carrier, with the remainder being isopropyl alcohol. The water content is more preferably in a range from about 20% to about 40% by volume of the carrier, and most preferably about 30% by volume of the carrier and wherein the isopropyl alcohol is included in an amount of about 70%. Embodiments of may include a carrier that comprises an alcohol, preferably isopropyl alcohol, at a concentration in a range from about 20% to about 90% by volume, preferably in a range from about 40% to about 85% by volume, and more preferably in a range from about 50% to about 80% by volume. The carrier may also include other solvents such as acetone, and the like.

An important issue when applying any treatment composition to mollucsum contagiosum warts is proper compliance by the user. Prior art treatments often take weeks or months before resolution and elimination of mollucsum contagiosum warts occurs. This alone can compromise effective compliance and treatment. In contrast, the anti-infective compositions disclosed herein can result in resolution and elimination of mollucsum contagiosum warts in a matter of days (e.g., 10 days or less, preferably 7 days or less, more preferably 5 days or less, most preferably 3 days or less). Resolution sometimes occurs after only a single application of the anti-infective composition, preferably using 5 applications or less, more preferably 4 applications or less, and most preferably 2 or 3 applications or less. It is readily apparent that use of the disclosed anti-infective compositions to treat mollucsum contagiosum warts can greatly increase patient compliance and the rate of success.

Highly penetrating compositions can be formulated, as a result of including a tissue-penetrating carrier, so as to penetrate quickly so that the treatment composition is no longer detected on the skin surface after less than about 1 minute, preferably less than about 40 seconds, more preferably less than about 30 seconds, and most preferably less than about 20 seconds. Viruses are deactivated and inflammatory agents are neutralized within minutes or seconds after effective penetration.

Benzocaine can further enhance patient compliance and efficacy of the anti-infective compositions. Examples of other topical anesthetics that may be used include butamben, dibucaine, lidocaine, oxybuprocaine, pramoxine, proparacaine, proxymetacaine, tetracaine, and mixtures thereof.

The carrier may also include other components that, by themselves, may be too viscous to act as tissue penetrating agents, but which, in combination with water, isopropyl alcohol, and other solvents identified herein or known to those of skill in the art, can penetrate tissue. Such components include ethoxylated alcohols (e.g., lauryl alcohol ethoxylates), ethoxylated nonylphenols (e.g., Nonoxynol-9), low molecular weight glycols (e.g., ranging from ethylene glycol to PEG-400, propylene glycol, propanediol, and the like), ethoxylated amines, and their quaternaries. Certain essential oils and emollients, which are normally water insoluble, can be made soluble in water by ethoxylation (e.g., ethoxylated lanolin).

Penetration inhibiting components include chemicals which are petrolatum based substances, materials conventionally utilized as thickeners, naturally occurring oils, substances derived from naturally occurring oils, or any other substance which is added primarily to increase the tendency of a treatment composition to remain on the surface of skin lesions. Example anti-infective compositions may include less than about 10% by weight of oils (e.g., tea tree oils, which some people use for treating molluscum contagiosum warts), preferably less than about 5% by weight of oils, more preferably than about 2% by weight of oils, and most preferably less than about 1% by weight of oils.

Treatment compositions may include other components that achieve a particular result and do not substantially reduce the ability of the treatment composition to penetrate into the disordered tissue or the ability of the treatment composition to be anti-infective. Examples of such components include pH adjusters, substances having anesthetic qualities, vasodilators, analgesics and defoamers. Example pH adjustors may include organic acids, mineral acids in minute amounts, organic bases or mineral bases also in minute amounts. Preservatives may be added to the anti-infective composition, including parabens, preferably methyl and propyl parabens. Preservatives, if present, are included in the composition in a range from about 0.0001% to about 0.01% by volume of the treatment composition.

Applicators may form part of a method and system for applying the anti-infective compositions. Examples of applicators include those taught in U.S. Pat. No. 5,709,866 (Booras et al.), U.S. Pat. No. 5,704,906 (Fox), U.S. Pat. No. 5,527,534 (Mythling), U.S. Pat. No. 5,016,651 (Stalcup et al.), U.S. Pat. No. 4,887,994 (Bedford), and U.S. Pat. No. 4,952,204 (Korteweg), the disclosures of which are incorporated herein by reference. Example applicators include prepackaged applicators with agitation pads impregnated with the anti-infective composition. An applicator may be provided as a unitary structure such as a sealed container that is frangible and configured for a single use.

Figure 2A:
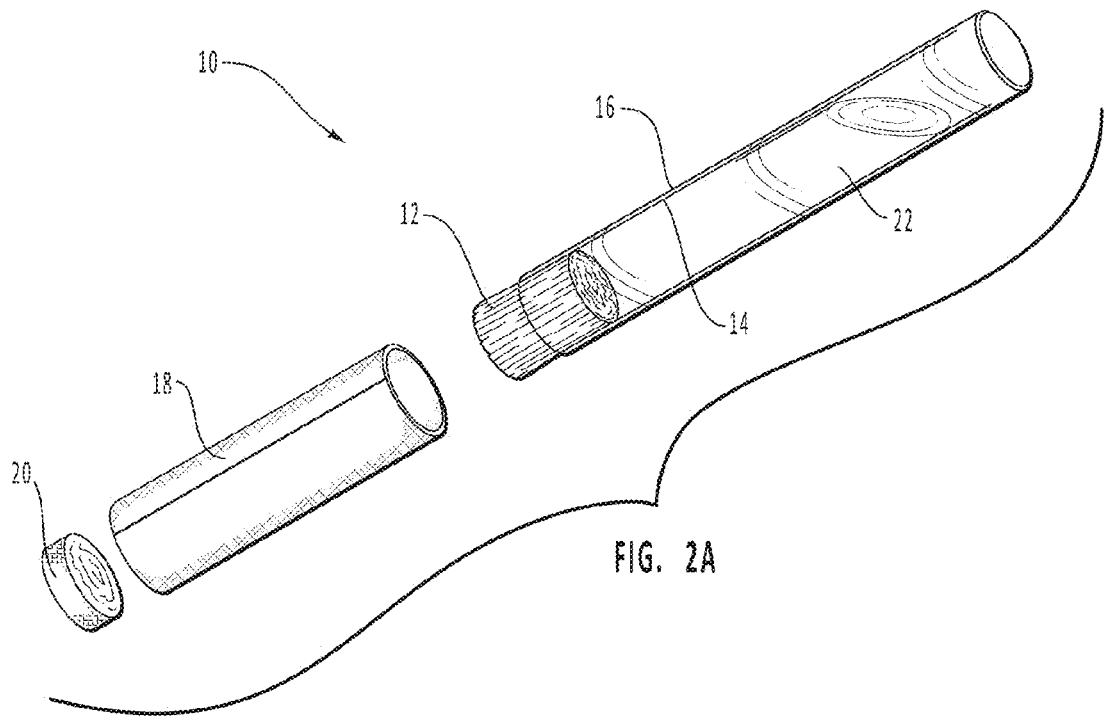
FIG. 2A is an exploded perspective view of an example applicator that contains the anti-infective composition.

FIGS. 2A-2E depict an example applicator 10. The details of applicator 10 are best seen in FIG. 2A, which is an exploded perspective view, FIG. 2B, which is a perspective view of the assembled applicator, and FIG. 2C as it appears when ready for application. Applicator 10 includes an absorbent pad 12 abutted against a frangible ampule or reservoir 14 via open delivery end 17 of the flexible container 16. Frangible reservoir 14 is housed in a container 16 that forms a holder for pad 12. Frangible reservoir is enclosed by pad 12, the sidewalls of container 16, and the closed end 19 of container 16. Frangible reservoir 14 is preferably a thin glass ampule, while container 16 is preferably formed from a flexible plastic. A protective sleeve 18 is provided, which is designed to keep pad 12 free from contamination until applicator 10 is ready for use on the disordered tissue. A cap 20 is provided to fit into sleeve 18. The anti-infective composition 22 is held in frangible reservoir 14 until such time as frangible reservoir 14 is broken.

Figure 2B:
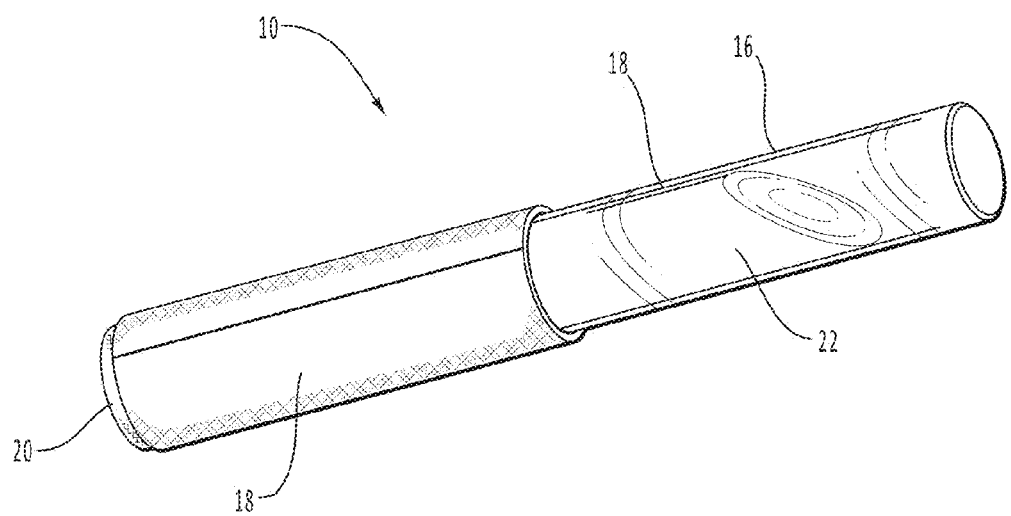
FIG. 2B is a perspective view of the example applicator depicted in FIG. 2A as it appears assembled prior to use.
Figures 2C, 2D:
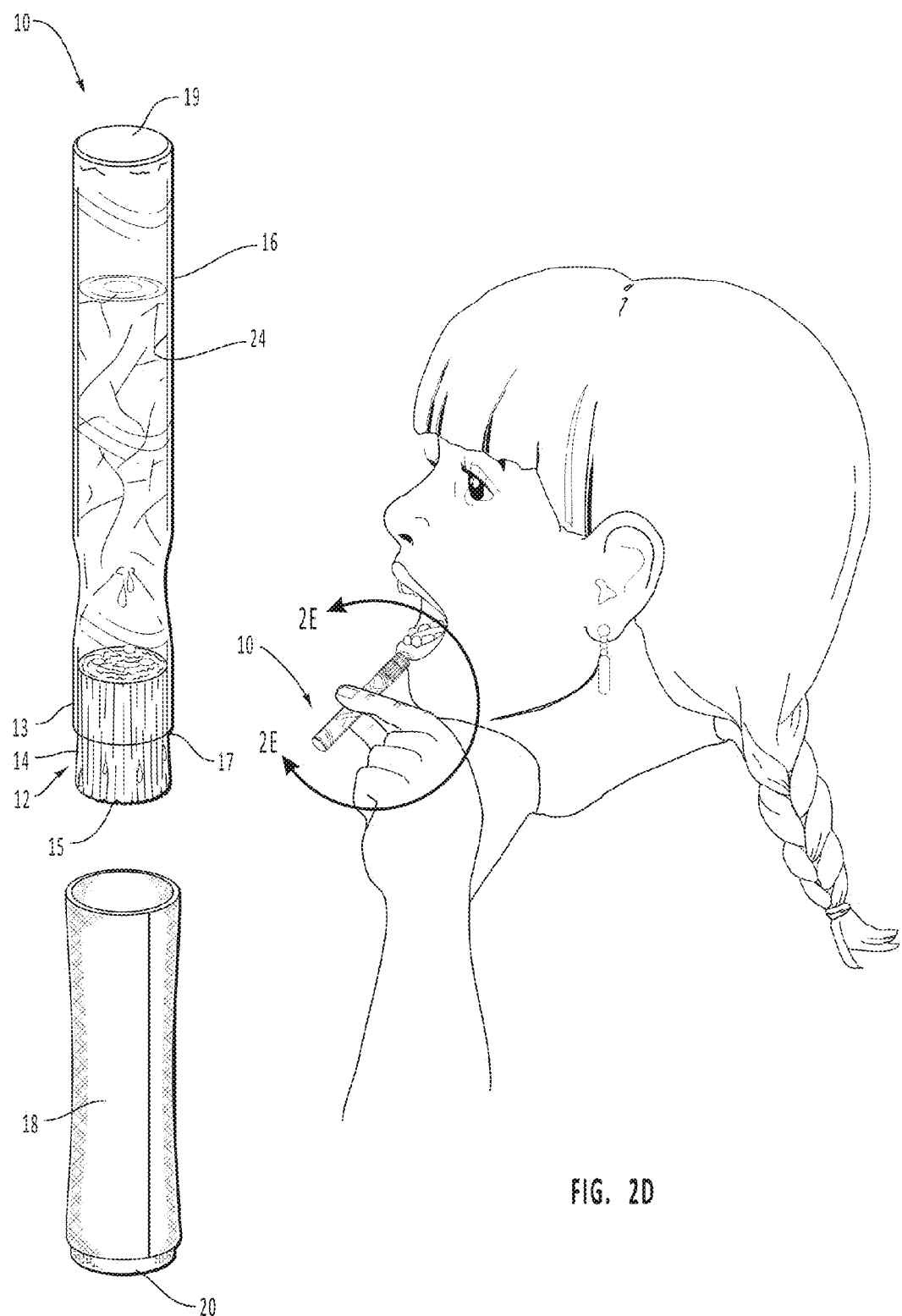
FIG. 2C is a perspective view of the example applicator depicted in FIG. 2B after the glass reservoir is crushed and the anti-infective composition is allowed to permeate the agitation pad.
FIG. 2D is a perspective view of an individual applying the anti-infective composition to one or more molluscum contagiosum warts.

FIG. 2C is a perspective view of the applicator depicted in FIG. 2B after frangible reservoir 14 has been ruptured. Anti-infective composition 22 is allowed to permeate pad 12 in preparation for application to warty tissue. In FIG. 2C, sleeve 18 has been removed to expose an impregnated pad 12. After impregnated pad 12 is sufficiently wetted, application to the warty tissue may commence.

Figure 2E:
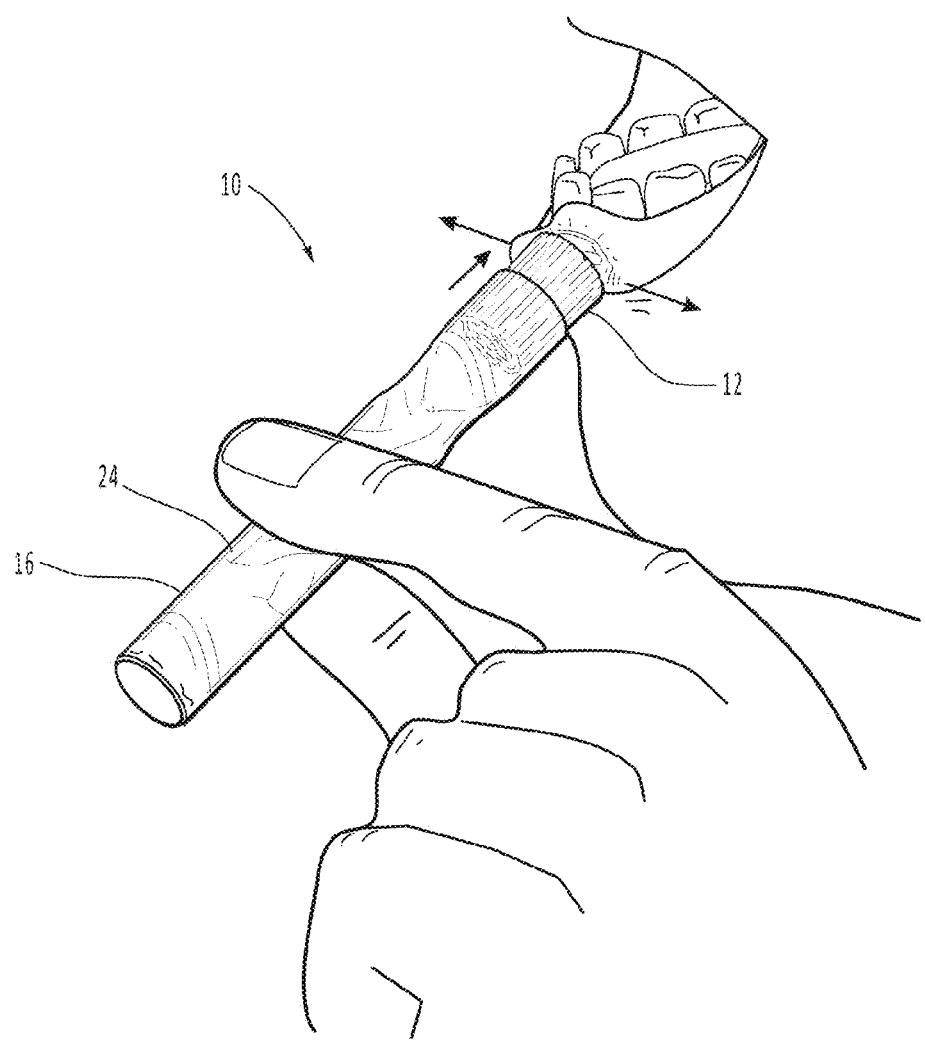
FIG. 2E is a detail taken along the section line 5-5 that depicts a close-up view of the inventive method.

FIG. 2D is a perspective view of an individual 26 applying treatment composition 22 to a molluscum contagiosum wart. FIG. 2E is a detail taken along the section line 2E-2E in FIG. 2D that depicts a close-up view of an example method of treatment. The detail view more clearly illustrates agitation of the molluscum contagiosum wart where impregnated pad 12 is being pressed into the wart in order to be firmly felt at the tissue underlying the molluscum contagiosum wart. The arrows illustrate directions of movement by way of example.

Once frangible reservoir 14 is ruptured the treatment composition is delivered to pad 12 as gravity enables it to flow into pad 12; however, rupturing frangible reservoir 14 creates shards of glass. Pad 12 prevents shards from passing and causing injury during delivery of the composition to the molluscum contagiosum wart. Another purpose of pad 12 is delivery of treatment composition. As discussed above, as pad 12 delivers the treatment composition it may be useful to also agitate and/or compress the tissue. Many configurations are available for pad 12, such as those disclosed in U.S. Pat. No. 1,822,566 and France Patent No. 2,700,698.

Figure 2F:
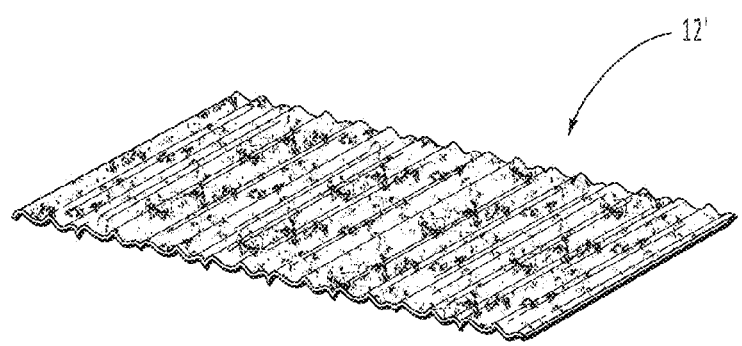
FIG. 2F shows a sheet of material before it is folded or collapsed to form an application pad.

Pad 12 is a folded sheet formed from a web of fibers. FIG. 2F depicts sheet 12' before it has been folded or collapsed to form pad 12. As shown in FIG. 2F, the sheet has a fluted appearance in order to provide an alignment such that when the sheet is gathered together in a bundle, it has longitudinal flutes. These longitudinal flutes provide a flow path for anti-infective composition 22 while the interlocked web of fibers can prevent shards of glass from passing out of container 16. Pad 12 has a configuration similar or identical to that of a cigarette filter. Examples of cigarette filters configurations that may be utilized are disclosed in U.S. Pat. No. 5,465,739 and U.S. Pat. No. 5,998,500, which are hereby incorporated by reference.

Pad 12 is preferably made of synthetic fibers that have a mesh which enables it to hold anti-infective composition 22 while having sufficient roughness to allow agitation of the warty tissue to enhance penetration by anti-infective composition 22. The fibers forming pad 12 are relatively densely positioned and can be relatively rigid. Pad 12 has a retention portion 13 positioned within flexible container 16. Retention portion 16 is can be attached to flexible container 16 through use of an appropriate adhesive that remains inert in the presence of the anti-infective composition or through heat fusing retention portion 13 with flexible container 16. Pad 12 also has a delivery portion 14 opposite from retention portion 16 that extends beyond open delivery end 17 of the flexible container 16. Regardless of the configuration of pad 12 or the material from which it is formed, the delivery portion is adapted to deliver the anti-infective composition to the warty tissue such that the composition is no longer visibly detectable on the warty tissue in less than about 1 minute after delivery of the anti-infective composition onto the warty tissue, preferably in less than about 40 seconds, more preferably in less than about 30 seconds, even more preferably in less than about 20 seconds, and most preferably in less than about 10 seconds.

Delivery portion 17 terminates at an application surface 15 that is relatively flat such that the warty tissue is uniformly contacted. Uniformly contacting the warty tissue with the flat application surface 15 reduces the risk of injuring the warty tissue as the tissue is contacted and agitated.

The retention portion of pad has a length that is sufficient for the pad to be securely anchored in the open delivery end of the container. The delivery portion has a length and sufficient rigidity to enable the application surface to optionally scrub the disordered tissue. When the pad is formed by folding or compressing together a sheet that is a polyester fiber web as shown in FIG. 2F at 12', the retention portion preferably has a length ranging from about 5 mm to about 7 mm and the delivery portion can have a length ranging from about 1 mm to about 5 mm. The length of the retention portion is more preferably about 6 mm and the length of the delivery portion is more preferably 4 mm. The diameter of the pad is preferably about 7 mm to about 1 cm, and is most preferably about 8 mm. This diameter is sufficiently large to enable large amounts of composition to be delivered and provides sufficient surface area to contact one or more molluscum contagiosum warts as needed. More particularly, a pad diameter that roughly corresponds with the diameter of a molluscum contagiosum wart in its various stages of development is ideally configured to agitate the treatment site.

In addition to a pad that is a folded sheet formed from a web of fibers, the pad may also be formed from a cluster of aligned bristles. Use of bristles having relatively small diameters is preferred to enable the cluster to scrub while minimizing potential injury to the warty tissue. For example, if the bristles are formed from nylon and are about 1 cm long so that the retention portion and the delivery portion are each about 5 mm long, the diameter may range from about 0.1 mm to about 0.2 mm, and is more preferably 0.15 mm.

An advantage of applicator 10 is that frangible reservoir 14 holds a relatively large volume of the anti-infective composition so that the composition is delivered in an amount that is relatively large compared with the surface area to be treated. Further, the delivery is rapidly achieved due to the design of applicator 10 without requiring rewetting of pad 12 as the anti-infective composition is continually delivered to pad 12 until it is all used. For example, frangible reservoir 14 may deliver about 0.2 ml to about 1 ml to an area that is no greater than about 1 $cm^2$. Accordingly, the volume to surface area ratio is preferably in a range from about 0.2 $ml/cm^2$ to about 1 $ml/cm^2$. Such quantities are ideally sufficient to saturate the warty lesion so that it is available as a protective bath in or around the nucleus.

Figure 3:
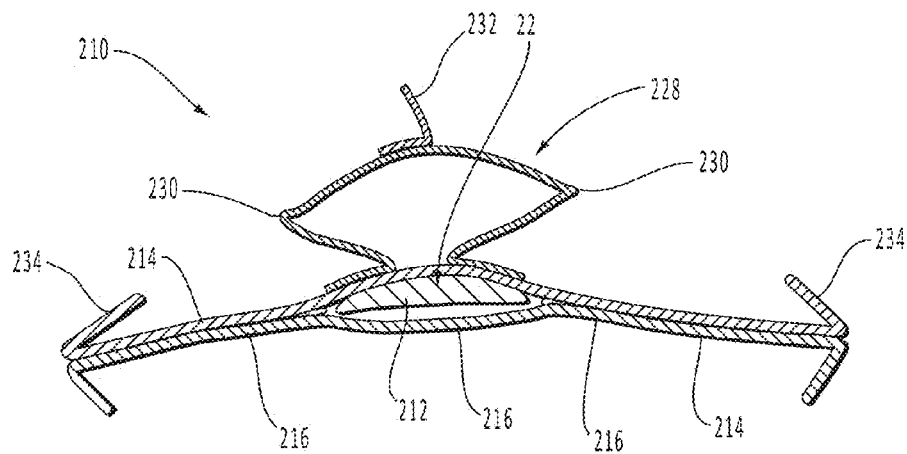
FIG. 3 is an elevational cross section view of an applicator that has a finger loop for vigorous topical irritation of the treatment site.

Another example applicator is illustrated in FIG. 3, which is a cross-sectional elevational view of an applicator 210 including an absorbent pad 212 that may be typical of a sterile adhesive bandage. Applicator 210 also includes adhesive wings 214 that may have adhesive typical of a sterile adhesive bandage. A separate strip acts as a container 216 in order to cause composition 22 to remain in pad 212 until container 216 is stripped away from adhesive wings 214 of applicator 210. In addition thereto, a finger loop 228 that may include finger loop folds 230, and a finger loop tab 232 is attached to applicator 210 immediately above pad 212. Finger loop 228 is configured to lie flat against adhesive wings 214 and can be opened by lifting on finger loop tab 232 and hinge open at finger loop folds 230. Applicator 210 may be applied to a treatment site as typical of a sterile adhesive bandage and left in place indefinitely. Additionally, after a selected time period of having applicator 210 on a treatment site, the medical professional or the patient may grasp the adhesive wing tabs 234 and gently them away from the skin. Meanwhile, the medical professional or the patient may insert a finger into finger loop 228, draw adhesive wings 214 toward finger loop 228, and commence treatment of molluscum contagiosum warty tissue.

Where it is desired to agitate warty tissue, applicator 210 may be applied at the point of pad 212 onto the tissue and then agitated against the tissue. Thereafter, applicator 210 may be discarded or adhesive wings 214 may be applied to the patient's skin to allow applicator 210 to remain over the warty tissue. This alternative may be preferable where bleeding is incidental to the inventive method. As such, applicator 210 doubles as an adhesive sterile bandage.

Figure 4:
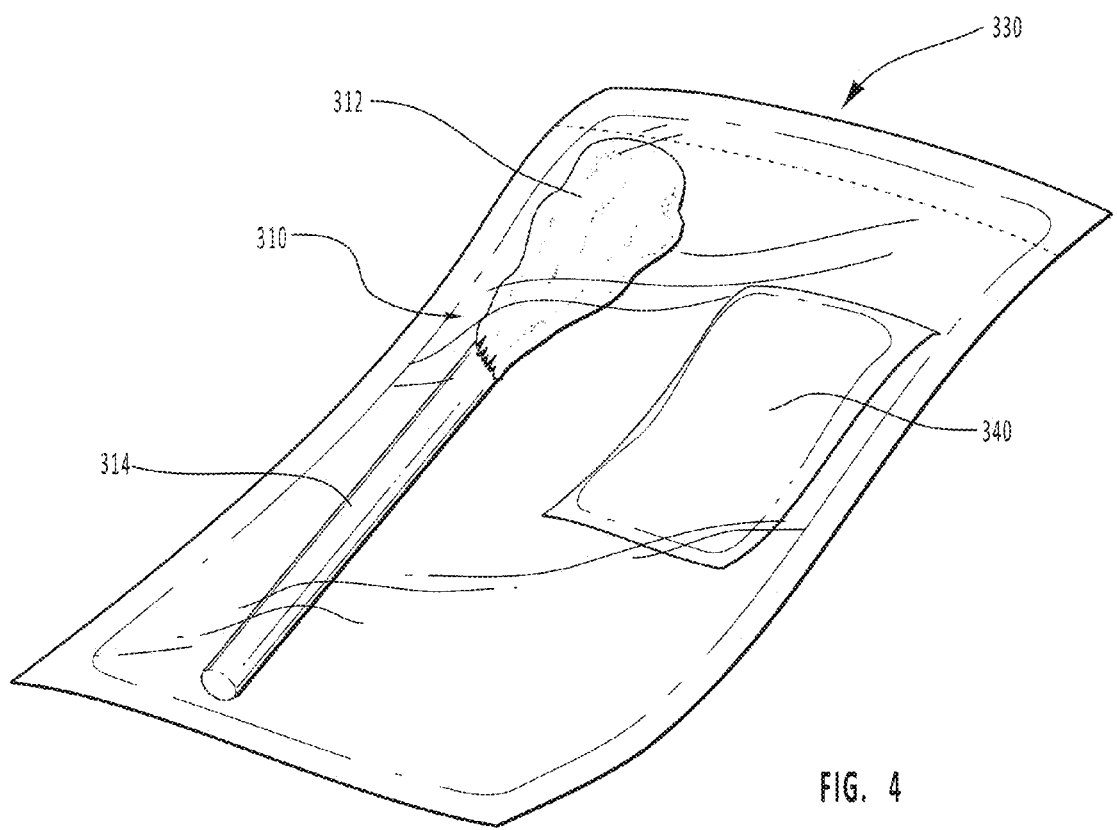
FIG. 4 is an elevational side view of an alternative applicator.

FIG. 4 is an elevational side view of an alternative applicator 310, which includes a swab agitation pad 312 upon a stem 314. Stem 314 may be formed from any suitable material; however, it is preferably relatively rigid to enable agitation pad 312 to be pushed and/or moved in the desired manner. It is preferable that swab agitation pad 312 be used under substantially sterile conditions so as to not introduce pathogenic elements into the warty tissue. The sterile agitation pad of the swab may be dipped into the treatment composition and used to gently abrade the skin. More preferably, the swab is held in a bag as shown at 330, which also holds a burst pouch as shown at 340. Burst pouch 340 holds the anti-infective composition and is sized and/or positioned within the bag such that upon bursting it can saturate the cotton swab. An example of a bag holding a swab and a burst pouch designed to be frangible is disclosed in U.S. Pat. No. 5,709,866 to Booras, previously referenced.

The swab agitation pad may be replaced with a sponge to gently agitate warty tissue. An example of a foam pad or sponge mounted on a stick such as stem 314 is disclosed in U.S. Pat. No. 4,887,994 to Bedford, previously referenced. Reference is made to Bedford, col. 2, ln. 44-46, to coarse foam pads. Coarse foam pads enable tissue to be more easily agitated through combined rubbing and application of an appropriate amount of pressure than softer foam pads.

Figure 5:
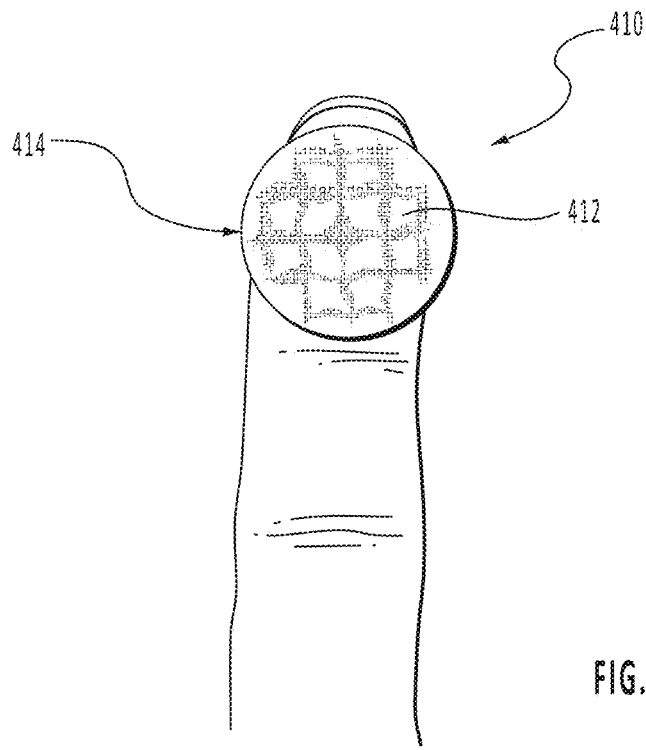
FIG. 5 is an elevational side view of an alternative example applicator that is fixed to a digit for vigorous topical agitation of the treatment site.

FIG. 5 is an elevational perspective view of a fingertip applicator 410, which includes an absorbent pad 412 held on an adhesive surface 414, which can be applied to a fingertip. Pad 412 may include an absorbent material for retaining the composition and it may contain fixed scrubbing elements to assist in agitating disordered tissue.

Figure 6:
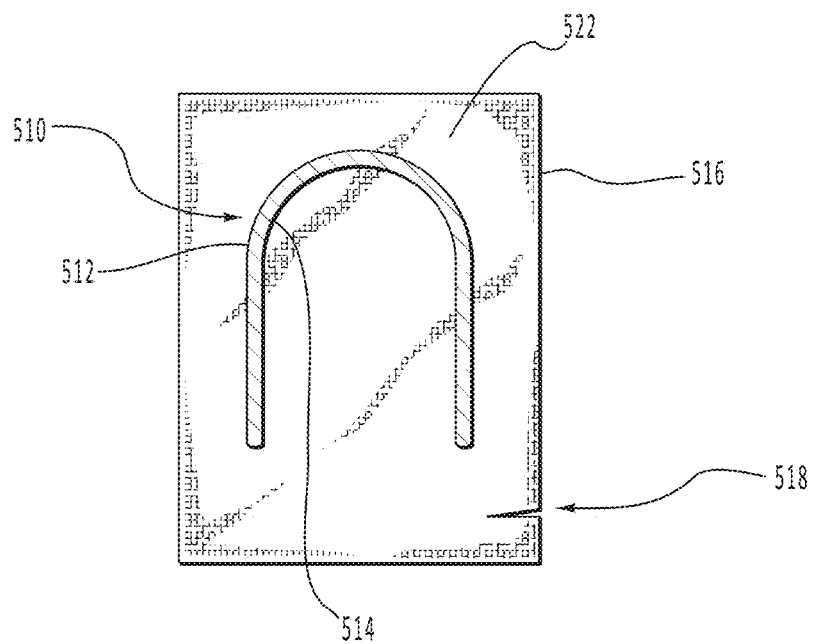
FIG. 6 is a cross-sectional plan view of an alternative example applicator that is placed over a digit and that is contained in a pre-wetted state before use.

FIG. 6 is an elevational cross-section view of a finger- or digit-container applicator 510, which includes an absorbent pad 512 with a first side 512 and a second side 514 that acts as a support. The user may rupture the container 516 such as by tearing a slit 518 and inserting a finger into applicator 510 against second side 514. Container 516 is a bag like that shown at 330 and may be referred to as what is commonly called a pillow pouch or package. Container 516 may also contain a burst pouch. Applicator 510 is preferably pre-moistened by composition 522 within container 516. Applicator may also be held in a container 516 in a dry sterile condition for dipping into a separate reservoir of the composition. First side 512 is made of an absorbent and mildly abrasive material that is substantially uniform in relation to the size of a disordered tissue site. First side 512 can approximate the roughness of a conventional gauze bandage or terry cloth and can be seamless and devoid of fabric folds. Additionally, where second side 514 is used to interface with a finger, it is a support for first side 512 as the delivery portion of applicator 510.

Applicator 510 can have varying sizes depending on its intended use. For example, if applicator 510 is used to deliver the anti-infective composition to a molluscum contagiosum wart or lesion it is large enough to permit entry of at least one fingertip into it. However, if applicator 510 is used to a cluster of molluscum contagiosum warts on, for example, an individual's arm, leg, back or stomach, it may be useful for applicator 510 to be large enough so that several fingers or even the entire hand can fit inside it like a mit. A mit-sized applicator enables the anti-infective composition to be rapidly delivered to a large surface area.

Figure 7:
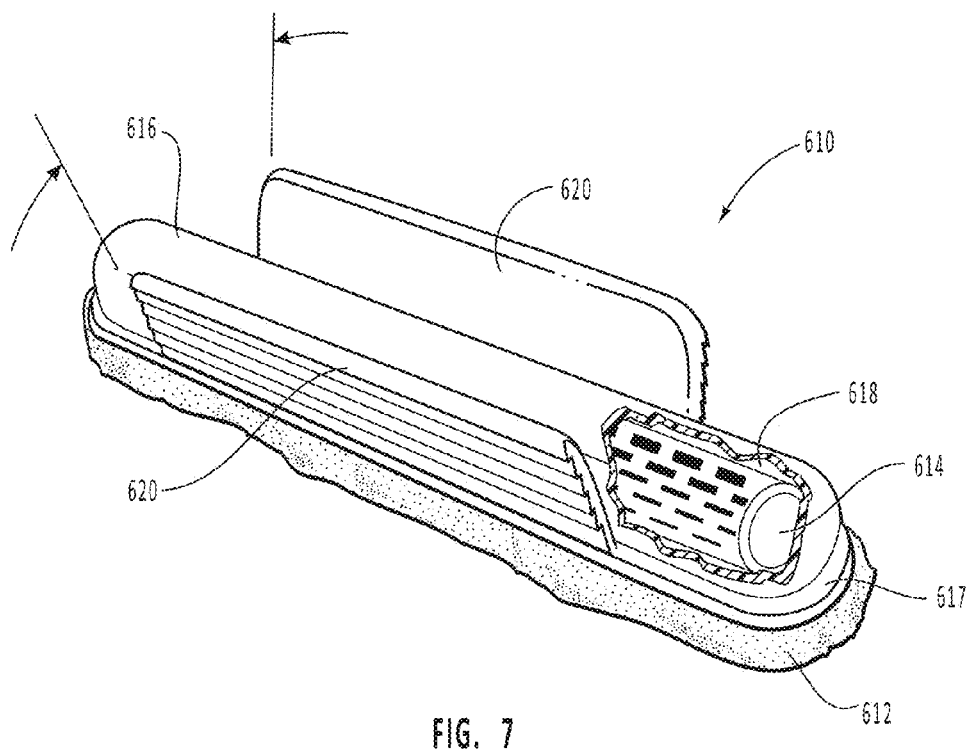
FIG. 7 is a perspective view with a partial break-away view of an alternative example applicator that is used to apply the anti-infective composition to large surface areas of the body.

FIG. 7 depicts another embodiment of a delivery system Like the mit sized version of applicator 510, applicator 610 is useful for treating large surfaces such as a patient's back. Applicator 610 comprises an anti-infective composition in a large frangible ampule 614 or reservoir, a container 616, and a pad 612. Container 616 has thin walls at recess 618, the closed end opposite from open delivery end 617, into which frangible ampule 614 is positioned. When applicator 610 is ready for use, handle wings 620 are squeezed until they compress the thin sidewalls of container 616 inward at recess 618 such that pressure is applied to frangible ampule 614 and ampule 614 ruptures. The anti-infective composition is then released and flows into pad 612. Frangible ampule 614 can contain a volume of anti-infective composition ranging from about 0.5 ml to about 4 ml, preferably from about 1.5 ml to about 3 ml, and more preferably from about 2 ml to about 3 ml.

Figure 8:
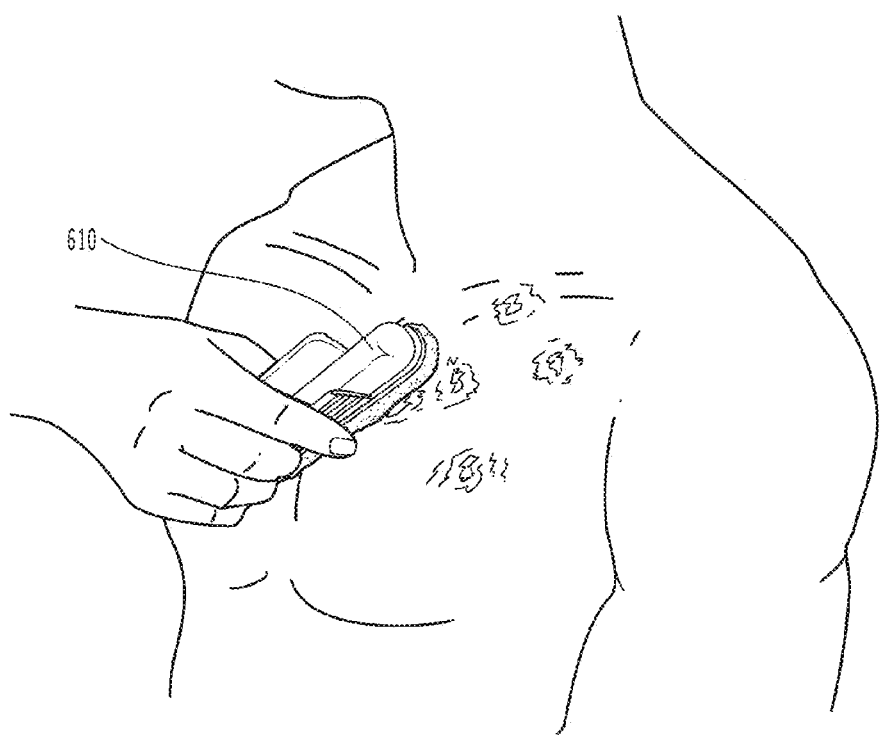
FIG. 8 is a perspective view of the example alternative applicator in FIG. 7 being used to apply the treatment composition to a relatively large outbreak of molluscum contagiosum warts on the chest area.

Pad 612 is adhered to the rim of open delivery end 617 of container 616 by suitable means, such as an adhesive, heat fusion, or a mechanically interlocked configuration. Pad 612 prevents shards from the rupture ampule from passing through and causing injury. Once pad 612 is adequately moistened, it can be used to rapidly apply anti-infective composition to large surface areas as shown in FIG. 8, which depicts the use of applicator 610 to apply the treatment composition to a patient's chest afflicted with a cluster of molluscum contagiosum warts. Applicator 610 can be used to merely deliver the anti-infective composition or it can be used to apply pressure and/or scrub the treatment area.

Figure 9:
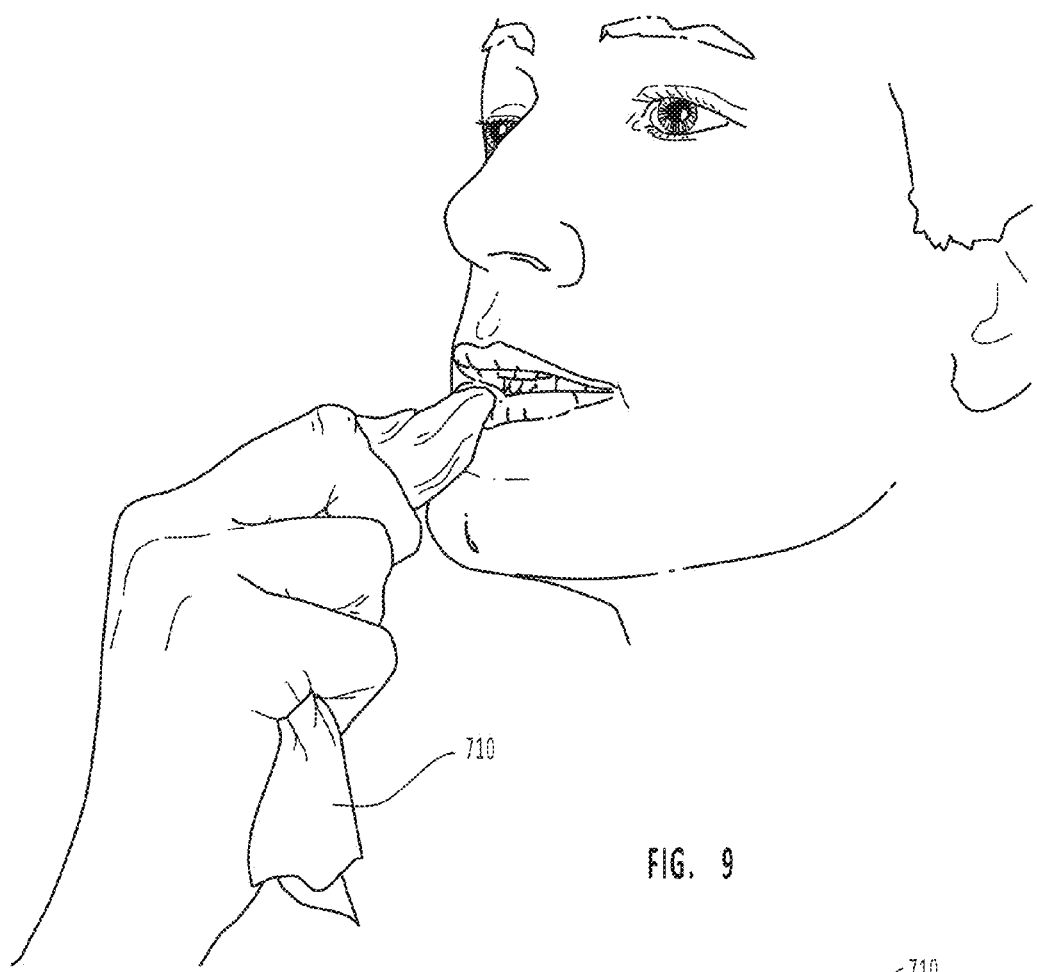
FIG. 9 is a perspective view of an example towelette used to apply the treatment composition to a cold sore.
Figure 10:
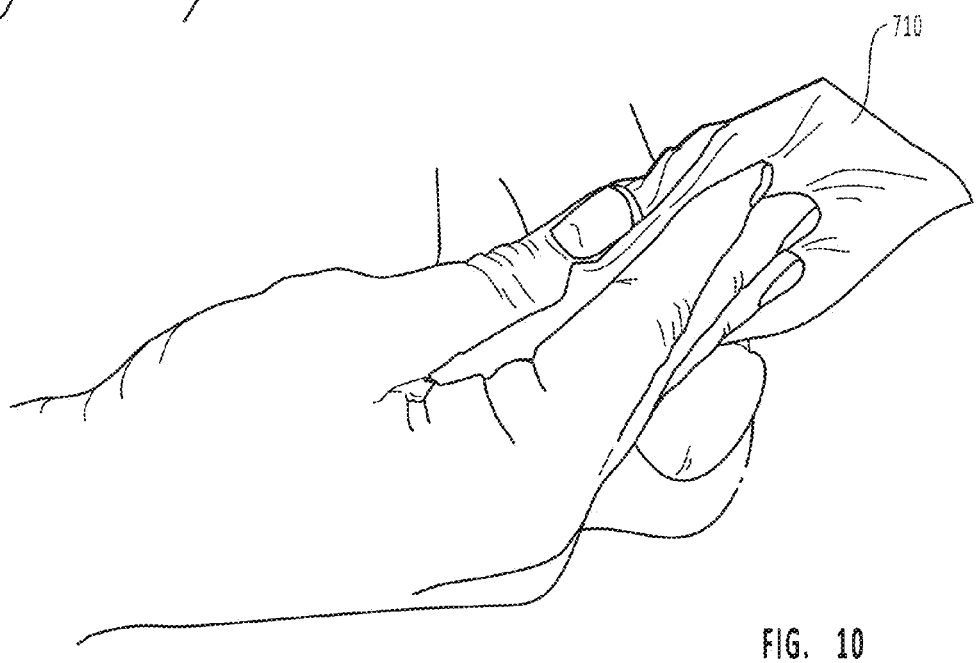
FIG. 10 is a perspective view of an example towelette used to apply the treatment composition to a sore on male genitalia.
Figure 11:
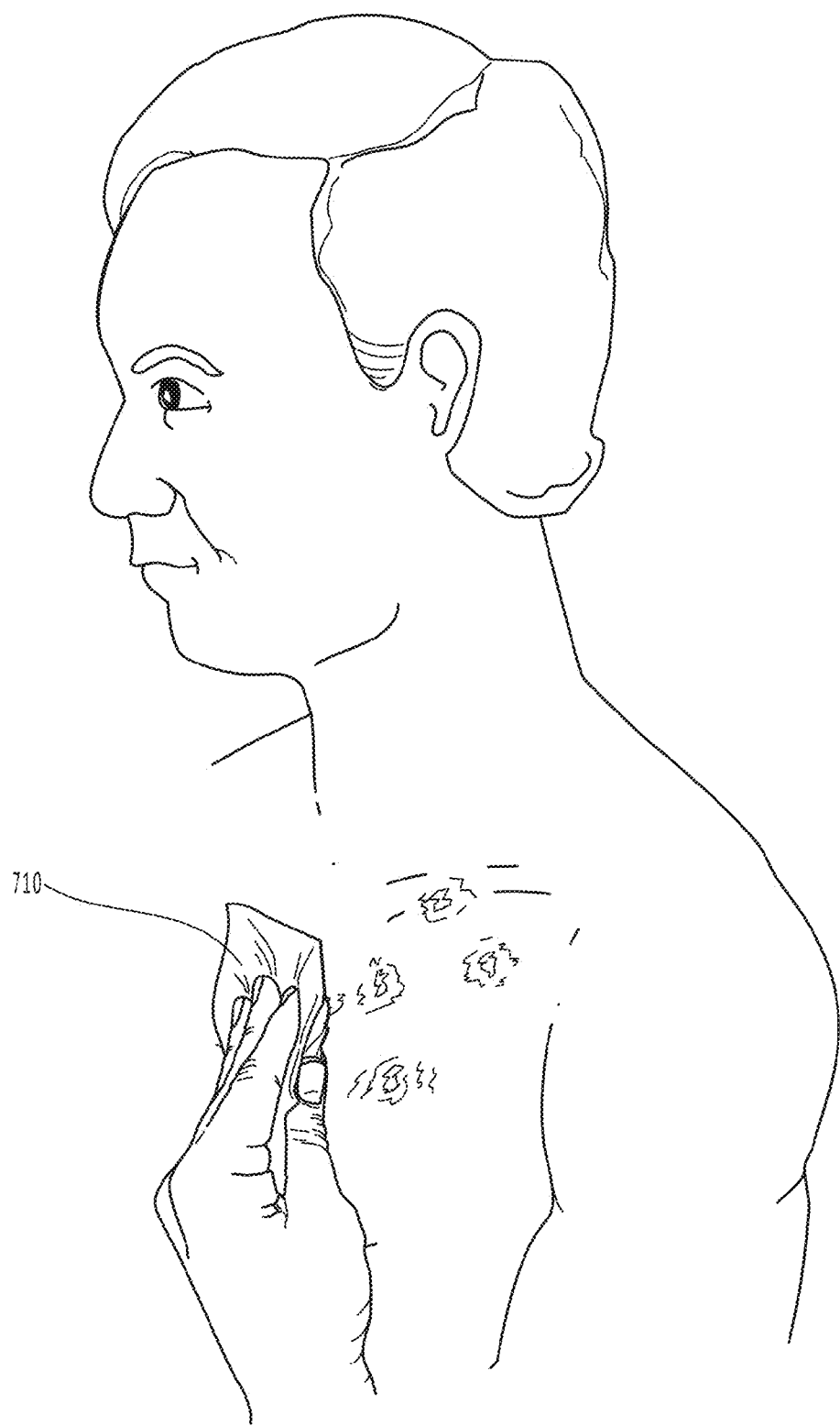
FIG. 11 is a perspective view of an example towelette used to apply the treatment composition to sores from shingles on the chest area.

FIGS. 9-11 depict a towelette being used as an applicator to treat molluscum contagiosum warts. The towelette depicted at 710 may be relatively smooth or relatively abrasive and can have varying thickness. The towelette can be repeatedly dipped to rewet it. For example, FIG. 9 depicts a user with a finger wrapped in a towelette used to deliver the anti-infective composition to a wart on the user's body. The towelette may be formed from fibers such as those discussed above in reference to applicator 10 or any of the other applicators. The towelette may be selected from existing stock formed from treated natural fibers, synthetic fibers, and untreated natural fibers and may be of woven or non-woven construction. One example of an abrasive towelette is a rough paper towel used in the paper towel industry or the like. One of ordinary skill in the art may select a towelette that has the preferred abrasive qualities while maintaining a preferred absorbability in order to convey the anti-infective composition to the treatment site.

FIG. 10 depicts towelette 710 being used in the genital area. An advantage of using a towelette for delivering the treatment composition in the genital area is that the towelette is able to conform to the various surface features and it enables the user to deliver the composition with sensitivity to the more sensitive parts in the genital area. As with the other applicators, the towelette is disposed of after a single use to prevent the spread of infective viruses to other parts of the patient's body.

FIG. 11 depicts towelette 710 being used to deliver the treatment composition to a patient that has a cluster of molluscum contagiosum on his chest. Towelettes are ideal for areas of the body that have surfaces areas that are not primarily flat or that have irregular surfaces.

The towelette may be held in a bag such as the bag shown at 330 which also holds a burst pouch as shown at 340. Burst pouch 340 holds the anti-infective composition and is sized and/or positioned within the bag such that upon bursting it saturates the towelette. The bag may hold the towelette and the burst pouch in a similar fashion to the designs disclosed in U.S. Pat. No. 5,709,866 to Booras, previously referenced. Towelette 710 may be dipped into a separate reservoir and then used to deliver the anti-infective composition.

Comparative Example 1

A 7-year old girl inflicted with soft wart-like and virtually colorless bumps was taken to a clinic and examined by a pediatrician. The pediatrician diagnosed the bumps as molluscum contagiosum warts and stated that there is no known cure for molluscum contagiosum warts but that some people have used tea tree oil to treat them. In view of this recommendation, a high quality tea tree oil was purchased from a local organic food store in Salt Lake City, Utah, and applied several times to the molluscum contagiosum warts. It had no effect on the molluscum contagiosum warts after several weeks of treatment.

Later, a dermatologist was consulted regarding possible treatments of molluscum contagiosum warts and provided the opinion that there is no known cure for molluscum contagiosum warts. The dermatologist further confirmed that tea tree oil was not proven to have any clinical effect on molluscum contagiosum warts.

Example 1

A treatment composition formulated for treating cold sores and sold under the name Viroxyn® had the following composition:

| | |
|---|---|
| Benzalkonium Chloride | 0.13% by weight |
| Liquid Carrier | 99.87% by weight |
| Isopropyl Alcohol 70% v/v | |
| Water 30% v/v | |

Even though both the pediatrician and dermatologist provided their professional opinions that there was no known cure for molluscum contagiosum warts, the cold sore medication was applied to one of the molluscum contagiosum warts on the 7-year old girl. Within 1-2 days the treated molluscum contagiosum wart turned black. Within 1-2 days after that, it fell off, leaving no trace or scar. Additional molluscum contagiosum warts on the girl were treated using the same composition with similar results: the warts turned black and fell off within a few days. Finally, one single remaining molluscum contagiosum wart on the underside of the girl that escaped detection, and which was particularly large and somewhat inflamed, was treated with the same composition. Within about 2-3 days, the wart turned into a scab and fell off, leaving no visible trace or scar. There has been no recurrence of molluscum contagiosum warts in the girl.

Hypothetical Examples

The following are hypothetical and are given by way of example in order to show other anti-infective compositions that may be used to treat molluscum contagiosum warts within the scope of the invention Example 2

| | |
|---|---|
| Benzocaine | 2.5% by weight |
| Benzalkonium Chloride | 0.13% by weight |
| Liquid Carrier (IPA + H2O) | 97.37% by weight |
| Isopropyl Alcohol 70% v/v | |
| Water 30% v/v | |

The composition of Example 2 is effective in treating molluscum contagiosum warts while the benzocaine reduces itching and inflammation to the person being treated. The benzocaine further enhances penetration of the composition into the molluscum contagiosum warts and maintains the composition in the nucleus, enhancing efficacy of the composition.

Example 3

| | |
|---|---|
| Benzocaine | 3% by weight |
| Benzalkonium Chloride | 0.13% by weight |
| Liquid Carrier (IPA + H2O) | 96.87% by weight |
| Isopropyl Alcohol 70% v/v | |
| Water 30% v/v | |

The composition of Example 3 is effective in treating molluscum contagiosum warts while the benzocaine reduces itching and inflammation to the person being treated. The benzocaine further enhances penetration of the composition into the molluscum contagiosum warts and maintains the composition in the nucleus, enhancing efficacy of the composition.

Example 4

| | |
|---|---|
| Benzocaine | 4% by weight |
| Benzalkonium Chloride | 0.13% by weight |
| Liquid Carrier (IPA + H2O) | 95.87% by weight |
| Isopropyl Alcohol 70% v/v | |
| Water 30% v/v | |

The composition of Example 4 is effective in treating molluscum contagiosum warts while the benzocaine reduces itching and inflammation to the person being treated. The benzocaine further enhances penetration of the composition into the molluscum contagiosum warts and maintains the composition in the nucleus, enhancing efficacy of the composition.

Example 5

| | |
|---|---|
| Benzocaine | 5% by weight |
| Benzalkonium Chloride | 0.13% by weight |
| Liquid Carrier (IPA + H2O) | 94.87% by weight |
| Isopropyl Alcohol 70% v/v | |
| Water 30% v/v | |

The composition of Example 5 is effective in treating molluscum contagiosum warts while the benzocaine reduces itching and inflammation to the person being treated. The benzocaine further enhances penetration of the composition into the molluscum contagiosum warts and maintains the composition in the nucleus, enhancing efficacy of the composition.

Example 6

| | |
|---|---|
| Benzocaine | 7.5% by weight |
| Benzalkonium Chloride | 0.13% by weight |
| Liquid Carrier (IPA + H2O) | 92.37% by weight |
| Isopropyl Alcohol 70% v/v | |
| Water 30% v/v | |

The composition of Example 6 is effective in treating molluscum contagiosum warts while the benzocaine reduces itching and inflammation to the person being treated. The benzocaine further enhances penetration of the composition into the molluscum contagiosum warts and maintains the composition in the nucleus, enhancing efficacy of the composition.

Example 7

Any of the foregoing examples is modified by substituting the identified liquid carrier with a liquid carrier comprised of 80%, 90% or 100% by volume isopropyl alcohol and/or an organic solvent that is more penetrating than isopropyl alcohol. The treatment compositions have even further enhanced penetration and can provide adequate penetration into warty molluscum contagiosum tissue.

Example 8

Any of the foregoing examples is modified by substituting the liquid carrier with a liquid carrier comprised of 60%, 50%, 40%, 30% or 20% by volume isopropyl alcohol and/or an organic solvent that is less penetrating than isopropyl alcohol.

Example 9

Any of the foregoing examples is modified so that the amount of benzalkonium chloride is included in an amount of 0.01%, 0.05%, 0.1%, 0.15%, 0.2%, 0.25%, 0.3%, 0.4% or 0.5% by weight.

Example 10

Any of the foregoing examples is modified by combining or substituting benzalkonium chloride with one or more of the following organohalides: benzethonium chloride, methyl benzethonium chloride, cetyl pyridinium chloride, chloroxylenol, hexachlorophene, triclosan, or chlorhexidine.

Example 11

Any of the foregoing examples is modified by combining or substituting benzalkonium chloride with one or more of the following organohalides: quaternary ammonium halide having an alkyl group with 6-18 carbons including mixtures of varied alkyl chains, ethoxylated quaternary ammonium halides including mixtures of alkyl chains, alkyl benzyl dimethyl ammonium halide, alkyl dimethyl ethyl benzyl ammonium halide, n-alkyl dimethyl benzyl ammonium halide, diisobutyl phenoxy ethoxy ethyl dimethyl benzyl ammonium halide, n-($C_{12}C_{14}C_{16}$) alkyl dimethyl benzyl ammonium halide, dodecyl dimethyl ammonium halide, dioctyl dimethyl ammonium halide, dialkyl dimethyl ammonium halide, dialkyl methyl benzyl ammonium halide, octyl decyl dimethyl ammonium halide, lauryl dimethyl benzyl ammonium halide, o-benzyl-p-chlorophenol, dideryl dimethyl ammonium halide, dioctyl dimethyl ammonium halide, or alkyl ($C_{14}C_{12}C_{16}$) dimethyl benzyl ammonium halide.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed is:

1. A method of treating a molluscum contagiosum wart, comprising: identifying a human with a molluscum contagiosum wart on the skin, wherein the molluscum contagiosum wart is caused by molluscum contagiosum virus and comprises warty tissue and a nucleus inside the warty tissue containing viruses;
topically applying an anti-infective composition to the molluscum contagiosum wart, the anti-infective composition comprising:
at least one anti-infective agent in a liquid carrier,
the anti-infective agent comprising an organohalide,
the liquid carrier comprising a tissue penetrating solvent for rapid penetration of the anti-infective agent into the molluscum contagiosum wart; and
causing or allowing the anti-infective composition to penetrate into the molluscum contagiosum wart, including through the warty tissue and into the nucleus of the wart,
the anti-infective composition killing viruses in the nucleus of the wart and causing the warty tissue to die and fall off the skin within 10 days or less;
wherein the organohalide is selected from the group consisting of benzethonium halide, methyl benzethonium halide, cetyl pyridinium halide, chloroxylenol, hexachlorophene, triclosan, chlorhexidine, quaternary ammonium halide compounds having an alkyl with 6-18 carbons, ethoxynlated quaternary ammonium halides, alkyl benzyl dimethyl ammonium halide, alkyl dimethyl ethyl benzyl ammonium halide, n-dialkyl methyl benzyl ammonium halide, n-alkyl dimethyl benzyl ammonium halide, diisobutyl phenoxy ethoxy ethyl dimethyl benzyl ammonium halide, n-($C_{12}C_{14}C_{16}$) alkyl dimethyl benzyl ammonium chloride, dodecyl dimethyl ammonium halide, dioctyl dimethyl ammonium halide, dialkyl dimethyl ammonium halide, dialkyl methyl benzyl ammonium halide, octyl decyl dimethyl ammonium halide, lauryl dimethyl benzyl ammonium halide, o-benzyl-p-chlorophenol, dodecyl dimethyl ammonium halide, dioctyl dimethyl ammonium halide, and alkyl ($C_{14}C_{12}C_{16}$) dimethyl benzyl ammonium halide.

2. The method of claim 1, wherein the at least one anti-infective agent comprises at least one quaternary ammonium chloride compound.

3. The method of claim 2, wherein the at least one quaternary ammonium chloride compound comprises benzalkonium chloride.

4. The method of claim 3, wherein the benzalkonium chloride is included in a concentration in a range from about 0.01% to about 0.5% by weight of the anti-infective composition.

5. The method of claim 3, wherein the benzalkonium chloride is included in a concentration in a range from about 0.05% to about 0.3% by weight of the anti-infective composition.

6. The method of claim 3, wherein the benzalkonium chloride is included in a concentration in a range from about 0.1% to about 0.2% by weight of the anti-infective composition.

7. The method of claim 3, wherein the benzalkonium chloride comprises benzalkonium chloride having an n-alkyl chain length that is at least one of $C_{12}$, $C_{14}$, $C_{16}$, or $C_{18}$.

8. The method of claim 1, wherein the anti-infective composition causes the one or more molluscum contagiosum warts to turn black and/or fall off the skin in 10 days or less.

9. The method of claim 1, wherein the anti-infective composition causes the one or more molluscum contagiosum warts to turn black and/or fall off the skin in 5 days or less.

10. The method of claim 1, wherein the anti-infective composition causes the one or more molluscum contagiosum warts to turn black and/or fall off the skin in 3 days or less.

11. The method of claim 1, wherein the tissue penetrating solvent comprises isopropyl alcohol and water, the isopropyl alcohol comprising from about 50% to about 80% by volume of the tissue penetrating solvent.

12. The method of claim 1, wherein the anti-infective composition further comprises a topical anesthetic.

13. The method of claim 12, wherein the topical anesthetic is included in an amount so as to enhance penetration of the anti-infective composition into the one or more molluscum contagiosum warts.

14. The method of claim 12, wherein the topical anesthetic comprises benzocaine.

15. The method of claim 1, wherein the anti-infective composition is not visibly detectable on the one or more molluscum contagiosum warts within about 1 minute or less after application.

16. The method of claim 1, wherein the anti-infective composition contains less than 10% of oils.

17. The method of claim 1, wherein the anti-infective composition contains less than 10% of tea tree oil.

18. A method of treating a molluscum contagiosum wart, comprising:
   identifying a human with a molluscum contagiosum wart on the skin, wherein the molluscum contagiosum wart is caused by molluscum contagiosum virus and comprises warty tissue and a nucleus inside the warty tissue containing viruses;
   applying an anti-infective composition to the molluscum contagiosum wart while applying pressure to or agitating the warty tissue to aid the anti-infective composition in penetrating into the warty tissue, the anti-infective composition comprising:
     at least one quaternary ammonium halide in a liquid carrier,
     the liquid carrier comprising a tissue penetrating solvent selected from methanol, ethanol, isopropyl alcohol, or acetone for rapid penetration of the anti-infective agent into the molluscum contagiosum wart so that the anti-infective composition has a viscosity that is not significantly greater than that of water and so that the anti-infective composition is not visibly detectable on the molluscum contagiosum wart within about 1 minute or less after application; and
   causing or allowing the anti-infective composition to penetrate into the molluscum contagiosum wart, including through the warty tissue and into the nucleus of the wart,
   the anti-infective composition killing viruses in the nucleus of the wart and causing the warty tissue to die and eventually fall off the skin.

19. A method of treating a molluscum contagiosum wart, comprising:
   identifying a human with a molluscum contagiosum wart on the skin, wherein the molluscum contagiosum wart is caused by molluscum contagiosum virus and comprises warty tissue and a nucleus inside the warty tissue containing viruses;
   applying an anti-infective composition to the molluscum contagiosum wart while applying pressure to or agitating the warty tissue to aid the anti-infective composition in penetrating into the warty tissue, the anti-infective composition comprising:
     at least one benzalkonium chloride compound in a liquid carrier,
     the liquid carrier comprising a tissue penetrating component for rapid penetration of the anti-infective agent into the molluscum contagiosum wart and containing less than 10% oil; and
   causing or allowing the anti-infective composition to penetrate into the molluscum contagiosum wart, including through the warty tissue and into the nucleus of the wart,
   the anti-infective composition killing viruses in the nucleus of the wart and causing the warty tissue to die and fall off the skin in 10 days or less.

* * * * *